(12) United States Patent
Chittenden et al.

(10) Patent No.: US 7,358,088 B2
(45) Date of Patent: Apr. 15, 2008

(54) PEPTIDES AND COMPOSITIONS WHICH MODULATE APOPTOSIS

(75) Inventors: Thomas D. Chittenden, Stow, MA (US); Robert J. Lutz, Wayland, MA (US)

(73) Assignee: ImmunoGen, Inc., Cambridge, MA (US)

( * ) Notice: Subject to any disclaimer, the term of this patent is extended or adjusted under 35 U.S.C. 154(b) by 0 days.

(21) Appl. No.: 11/501,910

(22) Filed: Aug. 10, 2006

(65) Prior Publication Data

US 2007/0081987 A1 Apr. 12, 2007

Related U.S. Application Data

(60) Division of application No. 09/828,870, filed on Apr. 10, 2001, now Pat. No. 7,097,982, which is a continuation of application No. 09/236,385, filed on Jan. 25, 1999, now Pat. No. 6,221,615, which is a continuation-in-part of application No. 08/908,597, filed on Aug. 8, 1997, now Pat. No. 5,863,795, which is a division of application No. 08/440,391, filed on May 12, 1995, now Pat. No. 5,656,725.

(51) Int. Cl.
*A61K 38/00* (2006.01)
*A61K 38/46* (2006.01)

(52) U.S. Cl. ............... 435/375; 530/350; 530/407; 514/2; 435/18; 435/23; 435/24; 435/7.1

(58) Field of Classification Search .............. 514/2; 435/7.1
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 5,015,568 | A | 5/1991 | Tsujimoto et al. |
| 5,202,429 | A | 4/1993 | Tsujimoto et al. |
| 5,283,173 | A | 2/1994 | Fields et al. |
| 5,656,725 | A | 8/1997 | Chittenden et al. |
| 5,672,686 | A | 9/1997 | Chittenden |
| 5,955,593 | A * | 9/1999 | Korsmeyer ......... 536/23.5 |
| 6,221,615 | B1 | 4/2001 | Chittenden et al. |

FOREIGN PATENT DOCUMENTS

WO    WO-9916787    4/1999

OTHER PUBLICATIONS

Fiebig et al. (2006) "Bcl-XL is qualitatively different from and ten times more effective than Bcl-2 when expressed in a breast cancer cell line", BMC Cancer. vol. 6, pp. 213-227.*
Abbas, A.K., et al., Celllular and Molecular Immunology, W.B. Saunders Co., Publisher, Philadelphia, PA (1991).
Ansel, H.C. and Popovich, N.G., Pharmaceutical Dosage Forms and Drug Delivery Systems, 5th Edition, Lea & Febiger, Publisher, Philadelphia, PA (1990).
Askew, D., et al., "Constitutive c-myc expression in an IL-3-dependent myeloid cell line supresses cell cycle arrest and accelerates apoptosis", Oncogene 6, pp. 1915-1922 (1991).
Austen, B.M. and Westwood, O.M.R., Protein Targeting and Secretion, IRL Press, Oxford (1991).
Bitterman, P.B., et al., "Repair after acute lung injury", Chest 105(3): 118S-121S (1994).
Blackburn, M. and Gait, M.J., Ed., Nucleic Acids in Chemistry and Biology, IRL Press, Oxford, England (1990).
Boise, L.H., et al., "bcl-x, a bcl-2-Related Gene That Functions as a Dominant Regulator of Apoptotic Cell Death", Cell, vol. 74, pp. 597-608 (1993).
Bradley, A., et al., "Modifying The Mouse: Design And Desire", Bio/Technology, vol. 10, pp. 534-539 (1992).
Campos, L.., et al., "Effects of *BCL-2* Antisense Oligodeoxynucleotides on In Vitro Proliferation and Survival of Normal Marrow Progenitorsand Leukemic Cells", Blood, vol. 84, pp. 595-600 (1994).
Carson, D.A., et al., "Apoptosis and disease", The Lancet, v341:1251-1254 (1993).
Casey, P., "Protein lipidation in cell signalling (Signal Transduction)", Science, 268: 221-225 (1995).
Chien, et al., "The two-hybrid system: A method to identify and clone genes for proteins that interact with a protein of interest", Proc. Natl. Acad. Sci., vol. 88, pp. 9578-9582 (1991).
Chittenden, T., et al., "A conserved domain in Bak, distinct from BH1 and BH2, mediates cell death and protein binding functions", EMBO Journal, vol. 14, No. 22, pp. 5589-5596 (1995).
Chittenden, T., et al., "Induction of apoptosis by the Bcl-2 homologue Bak", Nature, vol. 374, pp. 733-736 (1995).
Clarke, A.R., et al., "Thymocyte apoptosis induced by p53-dependent and independent pathways", Nature 362: 849-852 (1993).
Cohen, J.J., et al., "Apoptosis And Programmed Cell Death in Immunity", Annu. Rev. Immunol. 10: 267-293 (1992).
Debbas, M., et al., "Wild-type p53 mediates apoptosis by E1A, which is inhibited by E1B", Genes & Dev. 7: 546-554 (1993).
Dive, C., et al., "Drug-target interactions: only the first step in the commitment to a programmed cell death?" Br. J. Cancer, 64: 192-196 (1991).
Dole, et al., "Bcl-2 inihibits chemotherapy-induced apoptosis in neuroblastoma", Cancer Res., 54: 3253-3259 (1994).

(Continued)

*Primary Examiner*—Kathleen Kerr Bragdon
*Assistant Examiner*—Samuel Wei Liu
(74) *Attorney, Agent, or Firm*—Wilmer Cutler Pickering Hale and Dorr, LLP

(57) ABSTRACT

The present invention is directed to novel peptides and compositions capable of modulating apoptosis in cells, and to methods of modulating apoptosis employing the novel peptides and compositions of the invention. In one aspect, the invention is directed to a novel peptide designated the "GD domain," which is essential both to Bak's interaction with Bcl-$x_L$, and to Bak's cell killing function. Methods of identifying agonists or antagonists of GD domain function are provided. The GD domain is responsible for mediating key protein/protein interactions of significance to the actions of multiple cell death regulatory molecules.

6 Claims, 14 Drawing Sheets

OTHER PUBLICATIONS

Eastman, A., "Activation of Programmed Cell Death by Anticancer Agents: Cisplatin as a Model System", Cancel Cells, vol. 2, pp. 275-280 (1990).

Ellis, R.E., et al., "Mechanisms and Functions of Cell Death", Annu. Rev. Cell. Biol. 7: 663-698 (1991).

Erlich, H.A., Ed., PCR Technology: Principles and Applications for DNA Amplification, Stockton Press, New York, New York (1989).

Evan, G.I., et al., "Induction of Apoptosis in Fibroblasts by c-myc Protein", Cell, vol. 69, pp. 119-128 (1992).

Evans, B.E., et al., "Design of Nonpeptidal Ligands for a Peptide Receptor: Cholecystokinin Antagonists", J. Med. Chem., vol. 30, pp. 1229-1239 (1987).

Fanidi, A., et al., "Ccooperative interaction between c-*myc* and *bcl*-2 proto-oncogenes", Nature, vol. 359, pp. 554-556 (1992).

Fauchere, J., "Elements for the Rational Design of Peptide Drugs", Adv. Drug Res. 15: pp. 29-69 (1986).

Fisher, D.E., "Apoptosis in Cancer Therapy: Crossing the Threshold", Cell, vol. 78, pp. 539-542 (1994).

Fisher, T.C., et al., "*bcl*—2 Modulation of Apoptosis Induced by Anticancer Drugs: Resistance to Thymidylate Stress Is Independent of Classical Resistance Pathways", Cancer Res., 53: 3321-3326 (1993).

Germino, F.J., et al., "Screening for in vivo protein—protein interactions", Proc. Natl. Acad. Sci., vol. 90, pp. 933-937 (1993).

Guarenta, L., "Strategies for the identification of interacting proteins", Proc. Natl. Acad. Sci., vol. 90, pp. 1639-1641 (1993).

Haigh, A., et al., "Interference with the assembly of a virus-host transcription complex by peptide competition", Nature, vol. 344, pp. 257-259 (1990).

Harrington, E.A., et al., "c-Myc-induced apoptosis in fibroblasts is inhibited by specific cytokines", EMBO Journal, vol. 13, No. 14, pp. 3286-3295 (1994).

Henderson, S., et al., "Epstein-Barr virus-coded BHRF1 protein, a viral homologue of Bcl-2, protects human B cells from programmed cell death", Proc. Nat'l. Acad. Sci. USA, vol. 90, pp. 8479-8483 (1993).

Henderson, S., et al., "Induction of *bcl*-2 Expression by Epstein-Barr Virus Latent Membrane Protein 1 Protects Infected B Cells from Programmed Cell Death", Cell, vol. 65, pp. 1107-1115 (1991).

Hengartner, M.O., et al., "C. elegans Cell Survival Gene ced-9 Encodes a Functional Homolog of the Mammalian Proto-Oncogene bcl-2", Cell, vol. 76, pp. 665-676 (1994).

Hengartner, M.O., et al., "*Caenorhabditis elegans* gene *ced-9* protects cells from programmed cell death", Nature, vol. 356, pp. 494-499 (1992).

Hermeking, H., et al., "Mediation of c-Myc-Induced Apoptosis by p53", Science, vol. 265, pp. 2091-2093 (1994).

Hibner, U., et al., "Signaling of programmed cell death induction in WEHI-231 B. lymphoma cells", Eur. J. Immunol. 23(11): 2821-2825 (1993).

Hockenbery, D., et al., "Bcl-2 is an inner mitochondrial membrane protein that blocks programmed cell death", Nature, vol. 348, pp. 334-336 (1990).

Hockenbery, D.M., et al., "Bcl-2 Functions in an Antioxidant Pathway to Prevent Apoptosis", Cell, vol. 75, pp. 241-251 (1993).

Hockenbery, D.M., et al., "BCL2 protein is topographically restricted in tissues characterized by apoptotic cell death", Proc. Natl. Acad. Sci. USA, vol. 88, pp. 6961-6965 (1991).

Huang, Meng-Er, "A Possible Yeast Homolog of Human Active-Gene-Repairing Helicase ERCC6+." BBRC, vol. 201, No. 1. pp. 310-317. (1994).

Jones, J., Amino Acid and Peptide Synthesis, Oxford Science Publications, Oxford (1992).

Koh, D., et al., "Less Mortality but More Relapses in Experimental Allergic Encephalomyelitis in CD8-/- Mice", Science, vol. 256, pp. 1210-1213 (1992).

Korsmeyer, S.J., et al., "Bcl-2/Bax: a rheostat that regulates an anti-oxidant pathway and cell death", Cancer Biology, vol. 4, pp. 327-332 (1993).

Kozopas, K.M., et al., "MCL1, a gene expressed in programmed myeloid cell differentiation, has sequence similarity to BCL2", Proc. Natl. Acad. Sci. USA, vol. 90, pp. 3516-3520 (1993).

Kumar, S., et al., "Induction of apoptosis by the mouse *Nedd2* gene, which encodes a protein similar to the product of the *Caenorhabditis elegans* cell death gene *ced-3* and the mammalian IL-1β-converting enzyme", Genes Dev., 8: 1613-1626 (1994).

Lane, D.P., "A death in the life of p53", Nature, vol. 362, pp. 786-787 (1993).

Lehninger, A., Biochemistry, Second Edition, Worth Publishers, New York, NY (1975).

Lennon, S.V., et al., "Dose-dependent induction of apoptosis in human tumour cell lines by widely diverging stimuli", Cell Prolif., 24: pp. 203-214 (1991).

Levine, A.J., et al., "The p53 tumour suppressor gene", Nature, vol. 351, pp. 453-456 (1991).

Lin, E.Y., et al., "Characterization of A1, a Novel Hemopoietic-Specific Early-Response Gene with Sequence Similarity to *bcl-2* [1]", The Journal of Immunology, vol. 151, No. 4, pp. 1979-1988 (1993).

Lowe, S.W., et al., "p53 is required for radiation-induced apoptosis in mouse thymocytes", Nature, vol. 362, pp. 847-849 (1993).

Lowe, S.W., et al., "p53-Dependent Apoptosis Modulates the Cytotoxicity of Anticancer Agents", Cell, vol. 74, pp. 957-967 (1993).

McDonnell, T.J., et al., "bcl-2—Immunoglobulin Transgenic Mice Demonstrate Extended B Cell Survival and Follicular Lymphoproliferation", Cell, vol. 57, pp. 79-88 (1989).

McPherson, J.J., Ed., Directed Mutagenesis: A Practical Approach, IRL Press, Oxford (1991).

Melton, D.A., Ed., Antisense RNA and DNA, Cold Spring Harbour Laboratory Press, Cold Spring Harbor, New York (1988).

Miura, M., et al., "Induction of Apoptosis in Fibroblasts by IL-1β-Converting Enzyme, a Mammalian Homolog of the C. elegans Cell Death Gene ced3", Cell, vol. 75, pp. 653-660 (1993).

Miyashita and Reed, "Bcl-2 Oncoprotein Blocks Chemotherapy-Induced Apoptosis in a Human Leukemia Cell Line", Blood, vol. 81, pp. 151-157 (1993).

Neilan, J.G., et al., "An African Swine Fever Virus Gene with Similarity to the Proto-Oncogene *bcl-2* and the Epstein-Barr Virus Gene *BHRF1*", Journal of Virology, vol. 67, No. 7, pp. 4391-4394 (1993).

Oltvai, Z.N., et al., "Bcl-2 Heterodimerizes In Vivo with a Conserved Homolog, Bax, That Accelerates Programed Cell Death", Cell, vol. 74, pp. 609-619 (1993).

Oppenheim, R.W., "Cell Death During Development Of The Nervous System", Annu. Rev. Neurosci. 14: pp. 453-501 (1991).

Pilder, S., et al., "Deletion of the Gene Encoding the Adenovirus 5 Early Region 1B 21,000- Molecular-Weight Polypeptide Leads to Degradation of Viral and Host Cell DNA", J. Virol., vol. 52, pp. 664-671 (1984).

Raff, M.C., "Social controls on cell survival and cell death", Nature, vol. 356, pp. 397-400 (1992).

Rao, L., et al., "The adenovirus E1A proteins induce apoptosis, which is inhibited by the E1B 19-kDa and Bcl-2 proteins", Proc. Natl. Acad. Sci. USA, vol. 89, pp. 7742-7746 (1992).

Reed, J.C., "Bcl-2 and the Regulation of Programmed Cell Death", Journal of Cell Biology, vol. 124, pp. 1-6 (1994).

Reed, J.C., et al., "Antisense-mediated Inhibition of *BCL2* Protooncogene Expression and Leukemic Cell Growth and Survival: Comparisons of Phosphodiester and Phosphorothioate Oligodeoxynucleotides1", Cancer Research, 50, 6565-6570 (1990).

Robertson, E.J., Ed., Teratocarcinomas and Embryonic Stem Cells: A Practical Approach, IRL Press, Washington, DC (1987).

Sambrook, J., et al., Molecular Cloning: A Laboratory Manual, 2nd Ed., Cold Spring Harbor Laboratory Press, Planview, New York, (1989).

Sentman, C.L., et al., "bcl-2 Inihibits Multiple Forms of Apoptosis but Not Negative Selection in Thymocytes", Cell, vol. 67, pp. 879-888 (1991).

Smeyne, R.J., et al., "Continuous *c-fos* expression precedes programmed cell death in vivo", Nature, vol. 363, pp. 166-169 (1993).

Smith and Johnson, "Single-step purification of polypeptides expressed in *Escherichia coli* as fusions with glutathion *S*-transferase", Gene, 67: 31-40 (1988).

Speir, E., et al., "Potential Role of Human Cytomegalovirus and p53 Interaction in Coronary Restenosis", Science, vol. 265, pp. 391-394 (1994).

Stites, D.P. and Terr, A.I., Basic and Clinical Immunology, 7th Ed., Appleton & Lange, Publisher, Norwalk, CT (1991).

Strasser, A., et al., "bcl-2 Transgene Inhibits T Cell Death and Perturbs Thymic Self-Censorship", Cell, vol. 67, pp. 889-899 (1991).

Subramanian, T., et al., "19-kDa Tumor Antigen Coded by Early Region E1b of Adenovirus 2 Is Required for Efficient Synthesis and for Protection of Viral DNA", J. Biol. Chem., vol. 259, No. 19, pp. 11777-11783 (1984).

Tanaka, N., et al., "Cellular Commitment to Oncogene-Induced Transformation or Apoptosis Is Dependent on the Transcription Factor IRF-1", Cell, vol. 77, pp. 829-839 (1994).

Vaux, D.L., et al., "An Evolutionary Perspective on Apoptosis", Cell, vol. 76, pp. 777-779 (1994).

Vaux, D.L., et al., "*Bcl*-2 gene promotes Haemophoietic cell survival and cooperates with c-*myc* to immortalize pre-B cells", Nature, vol. 335, pp. 440-442 (1988).

Vaux, D.L., et al., "Prevention of programmed cell death in *Caenorhabditis elegans* by human bcl-2", Science, vol. 258, pp. 1955-1957 (1992).

Wang, I., et al., *Ich-1*, and *Ice/ced*-3-Related Gene, Encodes Both Positive and Negative Regulators of Programmed Cell Death, Cell, vol. 78, pp. 739-750 (1994).

White, B.A., Ed., "PCR Protocols: Current Methods and Applications", in Methods in Molecular Biology, Humana Press, Totowa, CT (1993).

Williams, G.T., "Programmed Cell Death: Apoptosis and Oncogenesis", Cell, vol. 65, pp. 1097-1098 (1991).

Williams, G.T., et al., "Molecular Regulation of Apoptosis: Genetic Controls on Cell Death", Cell, vol. 74, pp. 777-779 (1993).

Wu, X., et al., "p53 and E2F-1 cooperate to mediate apoptosis", Proc. Natl. Acad. Sci. USA, vol. 91, pp. 3602-3606 (1994).

Yin, X.M., et al., "BH1 and BH2 domains of Bcl-2 are required for inhibition of apoptosis and heterodimerization with Bax", Nature, vol. 369, pp. 321-323 (1994).

International Search Report for International Application No. PCT/US96/06122, dated Jul. 30, 1996.

Kieber-Emmons, et al., "Therapeutic peptides and peptidomimetics," Current Opinion in Biotechnology, vol. 8, pp. 435-441 (1997).

* cited by examiner

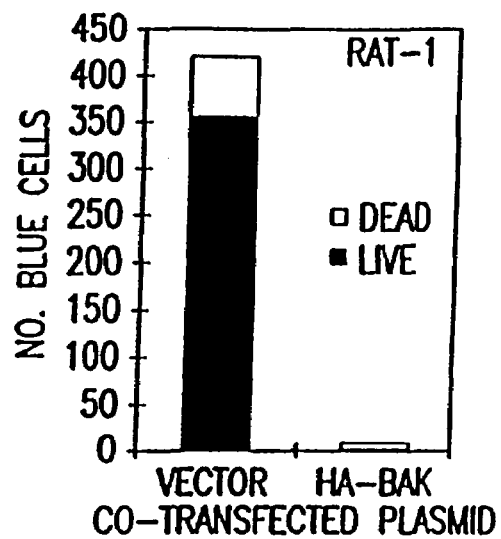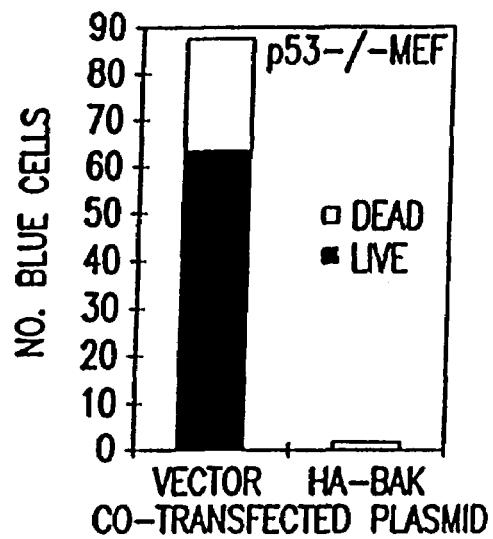
FIG.1A    FIG.1B
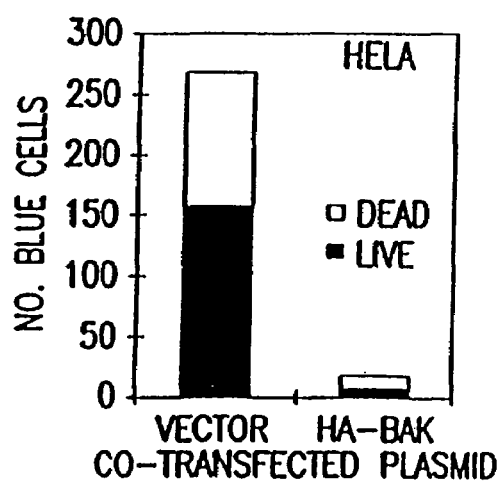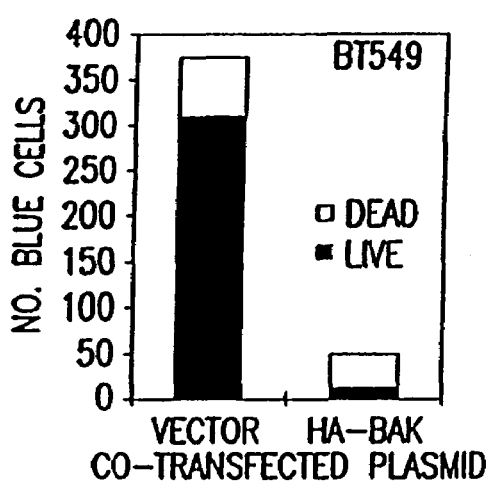
FIG.1C    FIG.1D

Interaction of Bak with GST-Bcl-$x_L$ in vitro

Interaction of Bak with Bcl-$x_L$ in COS cells

| PLASMID | RAT-1 CELL KILLING ACTIVITY | Bcl-XL BINDING ACTIVITY |
|---|---|---|
| Bak | + | + |
| Bak ΔPS | +/− | −/+ |
| Bak ΔGD | − | − |
| Bax | + | + |
| Bax ΔGD | − | − |
| Bip1a | + | + |
| Bip1a ΔGD | +/− | − |

FIG. 6

```
Bak
        220         230         240         250         260         270
         *           *           *           *           *           *
1.  CAG GTG GGA CGG CAG CTC GCC ATC ATC GGG GAC GAC ATC AAC CGA CGC TAT GAC TCA              [SEQ ID NO: 15]
 73  Q   V   G   R   Q   L   A   I   I   G   D   D   I   N   R   R   Y   D   S              [SEQ ID NO:  3]

280         290         300
         *           *           *
    GAG TTC CAG ACC ATG TTG CAG CAC CTG CAG CCC ACG
     E   F   Q   T   M   L   Q   H   L   Q   P   T       103

200         210         220         230         240         250
         *           *           *           *           *           *
2.  CCT AGC AGC ACC ATG GGG CAG GTG GGA CGG CAG CTC GCC ATC ATC GGG GAC GAC ATC              [SEQ ID NO: 17]
 67  P   S   S   T   M   G   Q   V   G   R   Q   L   A   I   I   G   D   D   I              [SEQ ID NO:  2]

260         270         280
         *           *           *
    AAC CGA CGC TAT GAC TCA GAG TTC CAG
     N   R   R   Y   D   S   E   F   Q       94

220         230         240         250         260
         *           *           *           *           *
3.  GTG GGA CGG CAG CTC GCC ATC ATC GGG GAC GAC ATC AAC CGA CGC                              [SEQ ID NO: 19]
 74  V   G   R   Q   L   A   I   I   G   D   D   I   N   R   R       88                     [SEQ ID NO: 10]
```

FIG. 8A

```
4.  82  GGG GAC GAC ATC AAC CGA CGC TAT GAC TCA GAG TTC CAG   94    [SEQ ID NO: 21]
         G   D   D   I   N   R   R   Y   D   S   E   F   Q          [SEQ ID NO: 1]
             250         260         270         280
              *           *           *           *

Bax
         160         170         180         190         200         210
          *           *           *           *           *           *
5.  52  CAG GAT GCG TCC ACC AAG AAG CTG AGC GAG TGT CTC AAG CGC ATC GGG GAC GAA CTG   71
         Q   D   A   S   T   K   K   L   S   E   C   L   K   R   I   G   D   E   L        [SEQ ID NO: 23]
                                                                                             [SEQ ID NO: 6]

180         190         200         210
          *           *           *           *
6.  59  CTG AGC GAG TGT CTC AAG CGC ATC GGG GAC GAA CTG GAC AGT AAC   73                  [SEQ ID NO: 25]
         L   S   E   C   L   K   R   I   G   D   E   L   D   S   N                        [SEQ ID NO: 4]
```

FIG. 8B

```
                     190          200          210
                       *            *            *
7.  CTC AAG CGC ATC GGG GAC GAA CTG GAC                              [SEQ ID NO: 27]
63  L   K   R   I   G   D   E   L   D                           21   [SEQ ID NO: 5]

Bipla
          150          160          170          180          190          200
            *            *            *            *            *            *
8.  TGC ATG GAG GGC AGT GAC GCA TTG GCC CTG CGG CTG GCC CTG CGG CTG GCC CTG CGC TGC ATC GGG GAC GAG ATG   [SEQ ID NO: 29]
50  C   M   E   G   S   D   A   L   A   L   R   L   A   L   R   L   A   C   I   G   D   E   M          [SEQ ID NO: 9]

210          220          230
            *            *            *
    GAC GTG AGC CTC AGG CCC CGC CTG                                                                       
    D   V   S   L   R   P   R   L                                                                   77

170          180          190          200          210
            *            *            *            *            *
9.  TTG GCC CTG CGG CTG GCC CTG CGC TGC ATC GGG GAC GAG ATG GAC GTG AGC                                  [SEQ ID NO: 31]
57  L   A   L   R   L   A   L   R   C   I   G   D   E   M   D   V   S                               21  [SEQ ID NO: 7]

190          200
            *            *
10. ATC GGG GAC GAG ATG                                                                                   [SEQ ID NO: 33]
64  I   G   D   E   M                                                                                68  [SEQ ID NO: 8]
```

FIG. 8C

PEPTIDES AND COMPOSITIONS WHICH MODULATE APOPTOSIS

CROSS-REFERENCE TO RELATED APPLICATIONS

This is a divisional application of U.S. patent application Ser. No. 09/828,870, filed Apr. 10, 2001, now U.S. Pat. No. 7,097,982, which is a continuation application of U.S. Application Ser. No. 09/236,385, filed 25 Jan. 1999, now U.S. Pat. No. 6,221,615, which in turn is a continuation-in-part of U.S. patent application Ser. No. 08/908,597 filed 8 Aug. 1997, now U.S. Pat. No. 5,863,795, which is a divisional application of U.S. Ser. No. 08/440,391, filed May 12, 1995, now U.S. Pat. No. 5,656,725.

FIELD OF THE INVENTION

The present invention relates generally to the field of cell physiology, and more particularly, to programmed cell death, or apoptosis. The novel peptides and compositions of the invention are useful for modulating apoptosis in cells.

BACKGROUND OF THE INVENTION

The phenomenon of programmed cell death, or "apoptosis," is known to be involved in and important to the normal course of a wide variety of developmental processes, including immune and nervous system maturation. Apoptosis also plays a role in adult tissues having high cell turnover rates (Ellis, R. E., et al., *Annu. Rev. Cell. Biol.* 7: 663-698 (1991); Oppenheim, R. W., *Annu. Rev. Neurosci.* 14: 453-501 (1991); Cohen, J. J., et al. *Annu. Rev. Immunol.* 10: 267-293 (1992); Raff, M. C., *Nature* 356: 397-400 (1992)). A number of different physiological signals normally activate programmed cell death in these contexts, but non-physiological insults, such as irradiation and exposure to drugs which damage DNA, also can trigger apoptosis (Eastman, A., *Cancer Cells* 2: 275-280 (1990); Dive, C., et al., *Br. J. Cancer* 64: 192-196 (1991); Lennon, S. V., et al., *Cell Prolif.* 24: 203-214 (1991)).

In addition to its role in development, apoptosis has been implicated as an important cellular safeguard against tumorigenesis (Williams, G. T., *Cell* 65: 1097-1098 (1991); Lane, D. P., *Nature* 362: 786-787 (1993)). Under certain conditions, cells die by apoptosis in response to high-level or deregulated expression of oncogenes (Askew, D., et al., *Oncogene* 6: 1915-1922 (1991); Evan, G. I., et al., *Cell* 69: 119-128 (1992); Rao, L., et al., *Proc. Natl. Acad. Sci. USA* 89: 7742-7746 (1992); Smeyne, R. J., et al., *Nature* 363: 166-169 (1993); Tanaka, S., et al., *Cell* 77: 829-839 (1994); Wu, X., et al., *Proc. Natl. Acad. Sci. USA* 91: 3602-3606 (1994)). Suppression of the apoptotic program, by a variety of genetic lesions, may contribute to the development and progression of malignancies. This is well illustrated by the frequent mutation of the p53 tumor suppressor gene in human tumors (Levine, A. J., et al., *Nature* 351: 453-456 (1991)). Wild-type p53 is required for efficient induction of apoptosis following DNA damage (Clarke, A. R., et al., *Nature* 362: 849-852 (1993); Lowe, S. W., et al., *Cell* 74: 957-967 (1993); Lowe, S. W., et al., *Nature* 362: 847-849 (1993)) and cell death induced by constitutive expression of certain oncogenes (Debbas, M., et al., *Genes & Dev.* 7: 546-554 (1993); Hermeking, H., et al., *Science* 265: 2091-2093 (1994); Tanaka, S., et al., *Cell* 77: 829-839 (1994); Wu, X., et al., *Natl. Acad. Sci. USA* 91: 3602-3606 (1994)). The cytotoxicity of many commonly used chemotherapeutic agents is mediated by wild-type p53 (Lowe, S. W., et al., *Cell* 74: 957-967 (1993); Fisher, D. E., *Cell* 78: 539-542 (1994)). Thus, loss of p53 function may contribute to the clinically significant problem of drug resistant tumor cells emerging following chemotherapy regimens.

The expression product of the bcl-2 oncogene functions as a potent suppressor of apoptotic cell death (McDonnell, T. J., et al., *Cell* 57: 79-88 (1989); Hockenbery, D., et al., *Nature* 348: 334-336 (1990)). Constitutive Bcl-2 expression can suppress apoptosis triggered by diverse stimuli, including growth factor withdrawal, oncogene expression, DNA damage, and oxidative stress (Vaux, D. L., et al., *Nature* 335: 440-442 (1988); Sentman, C. L., et al., *Cell* 67: 879-888 (1991); Strasser, A., et al., *Cell* 67: 889-899 (1991); Fanidi, A., et al., *Nature* 359: 554-556 (1992); Hockenbery, D. M., et al., *Cell* 75: 241-251 (1993)). There is also conservation of Bcl-2 function across species. For example, the ced-9 gene of the nematode *C. elegans* appears to be a structural and functional homolog of bcl-2 (Hengartner, M. O., et al., *Cell* 76: 665-676 (1994)) and bcl-2 can complement ced-9 mutations in transgenic animals (Vaux, D. L., et al., *Science* 258: 1955-1957 (1991)). These observations suggest that Bcl-2 is intimately connected with an evolutionarily conserved cell death program.

It is known that bcl-2 is a member of a family of related genes, at least some of which also modulate apoptosis of these, bcl-x bears the highest degree of homology to bcl-2, and is differentially spliced to produce a long form, termed bcl-$x_L$, and a shorter form, bcl-$x_S$, harboring an internal deletion (Boise, L. H., et al., *Cell* 74: 597-608 (1993)). Bcl-$x_L$, functions to suppress apoptosis, whereas the deleted form, Bcl-$x_S$, inhibits the protection against cell death provided by Bcl-2 expression. A second Bcl-2 homolog, Bax, forms heterodimers with Bcl-2 (Oltvai, Z. N., et al., *Cell* 74: 609-619 (1993)) and has been shown to counteract Bcl-2 and accelerate apoptosis. Mutational analysis of Bcl-2 has suggested that the interaction with Bax is required for Bcl-2 to function as an inhibitor of cell death (Yin, X. -M., et al., *Nature* 369: 321-323 (1994)).

The isolation and characterization of a bcl-2 related gene, termed bak, is described in co-pending U.S. application Ser. No. 08/321,071, filed 11 Oct. 1994, which is a continuation-in-part of U.S. application Ser. No. 08/287,427, filed 9 Aug. 1994 (bak is referred to therein as bcl-y), the disclosures of which are incorporated herein by reference. Ectopic Bak expression accelerates the death of an IL-3 dependent cell line upon cytokine withdrawal, and opposes the protection against apoptosis afforded by Bcl-2. In addition, enforced expression of Bak is sufficient to induce apoptosis of serum deprived fibroblasts, raising the possibility that Bak directly activates, or is itself a component of, the cell death machinery.

The known cellular Bcl-2 related genes, where analyzed, have distinct patterns of expression and thus may function in different tissues. While Bcl-2 expression appears to be required for maintenance of the mature immune system, it is desirable to identify other genes which may govern apoptotic cell death in other lineages. In addition, the identification of particular regions or domains of the proteins encoded by such genes may provide a basis for understanding their structural and functional characteristics and allow the development of valuable diagnostics and therapeutics. For example, the identification of agents capable of restoring or inducing apoptosis in tumor cells (in which loss of p53 tumor suppressor gene function may be implicated in tumorigenesis and in clinically significant drug resistance) would be of significant therapeutic value, particularly where such restoration or induction was independent of p53 function. Similarly, the development of agents capable of counteracting the anti-apoptotic function of oncogenes such as bcl-2, the activation of which is implicated in tumorigenesis (e.g., lymphoma) and in chemotherapeutic drug resistance, would be of great potential value.

SUMMARY OF THE INVENTION

The present invention is directed to a novel protein domain of general significance to the actions of multiple cell death regulatory molecules, which has been identified and mapped to a short subsequence in the central portion of the Bak molecule. This heretofore unrecognized protein domain, which the inventor has designated the "GD domain," is essential both to Bak's interaction with Bcl-$x_L$, and to Bak's cell killing function. Truncated Bak species encompassing the GD domain are themselves sufficient to bind to Bcl-$x_L$ and to kill cells in transfection assays.

The GD domain has been identified in two other Bcl-2 binding proteins that function to induce apoptosis: Bax and Bip1a. As with Bak, mutation of the homologous GD domain elements in Bax and Bip1a diminishes cell killing and protein binding function. Thus, the GD domain is responsible for mediating key protein/protein interactions of significance to the actions of multiple cell death regulatory molecules.

In one aspect, then, the invention is directed to purified and isolated peptides comprising the GD domain and to molecules that mimic its structure and/or function, useful for inducing or modulating the apoptotic state of a cell. Chemical compounds that disrupt the function of the GD domain have utility as apoptosis-modulating agents. Accordingly, in another aspect, the invention is directed to agents capable of disrupting GD domain function. Such agents include, but are not limited to, molecules that bind to the GD domain, molecules that interfere with the interaction of the GD domain with other protein(s), and molecules comprising the GD domain which is altered in some manner. The invention provides methods to identify molecules that modulate apoptosis by disrupting the function of the GD domain, which accordingly comprise additional contemplated embodiments.

In additional aspects, the present invention relates to products and processes involved in the cloning, preparation and expression of peptides comprising the GD domain; antibodies with specificity to the GD domain; and nucleotide sequences encoding the GD domain or portions thereof. Peptides comprising the GD domain are useful for producing antibodies thereto. Such antibodies are useful for detecting and isolating proteins comprising the GD domain in biological specimens including, for example, cells from all human tissues including heart tissue, lung tissue, tumor cells, brain tissue, placenta, liver, skeletal muscle, kidney, and pancreas, as well as for modulating the apoptotic activity of proteins comprising the GD domain in and from such biological specimens, and constitute additional aspects of the invention.

In yet another aspect, the invention provides for expression vectors containing genetic sequences, hosts transformed with such expression vectors, and methods for producing the recombinant GD domain peptides of the invention.

The present invention is further directed to methods for inducing or suppressing apoptosis in the cells and/or tissues of individuals suffering from degenerative disorders characterized by inappropriate cell proliferation or inappropriate cell death, respectively. Degenerative disorders characterized by inappropriate cell proliferation include, for example, inflammatory conditions, cancer, including lymphomas, such as prostate hyperplasia, genotypic tumors, etc. Degenerative disorders characterized by inappropriate cell death include, for example, autoimmune diseases, acquired immunodeficiency disease (AIDS), cell death due to radiation therapy or chemotherapy, neurodegenerative diseases, such as Alzheimer's disease and Parkinson's disease, etc.

The present invention also relates to methods for detecting the presence of the GD domain peptide, as well as methods directed to the diagnosis of degenerative disorders, which disorders are associated with an increased or decreased level of expression of proteins comprising the GD domain, as compared to the expected level of expression of such proteins in the normal cell population.

The present invention relates to the therapeutic use of peptides comprising the GD domain.

The present invention also relates to methods for modulating the apoptotic state of a cell by administering peptides comprising the GD domain peptide, or mutants thereof, to an individual suffering from a degenerative disorder characterized by inappropriate cell proliferation or inappropriate cell death, in order to stabilize inappropriate cell proliferation (i.e., induce apoptosis) or stabilize inappropriate cell death (i.e., suppress apoptosis), respectively, and/or in either case to restore normal cell behavior.

In another aspect, the present invention is related to the surprising discovery that the Bak GD domain is involved in and sufficient for homodimerization and heterodimerization of Bak. Nonlimiting examples of Bak GD domain dimerization include Bak (homodimerization), Bax (heterodimerization with a different killer protein) and Bcl-$x_L$ (heterodimerization with a survival protein). Further, it has unexpectedly been discovered that the non-essential regions of the Bak protein in this aspect include the two domains in the carboxyl terminal half of the protein that show the highest degree of homology to other Bcl-2 family members (Bcl-2 homology domains I and II). Thus, peptides comprising the GD domain are capable of mediating interactions not only with Bcl-$x_L$, but also with Bak and Bax.

These and other objects and aspects of the invention will be apparent to those of skill from the description which follows.

BRIEF DESCRIPTION OF THE FIGURES

FIGS. 1A-1D. Cell killing function of Bak in different cell lines.

A. Rat-1 cells were co-transfected with a β-galactosidase marker plasmid in combination with either a control plasmid (vector), or a plasmid expressing HA-epitope tagged Bak (HA-Bak). Cells were fixed and stained with X-gal at 24 hours post-transfection, and the number of blue cells (β-galactosidase-positive) counted by microscopic examination.

B. Mouse Embryonic Fibroblasts (MEF) lacking functional p53 (p53$^{-/-}$MEF) were co-transfected as described in(A).

C. Hela cells, derived from cervical carcinoma, were co-transfected as described in (A).

D. BT549 cells, derived from breast carcinoma, were co-transfected as described in (A).

Figure 2:
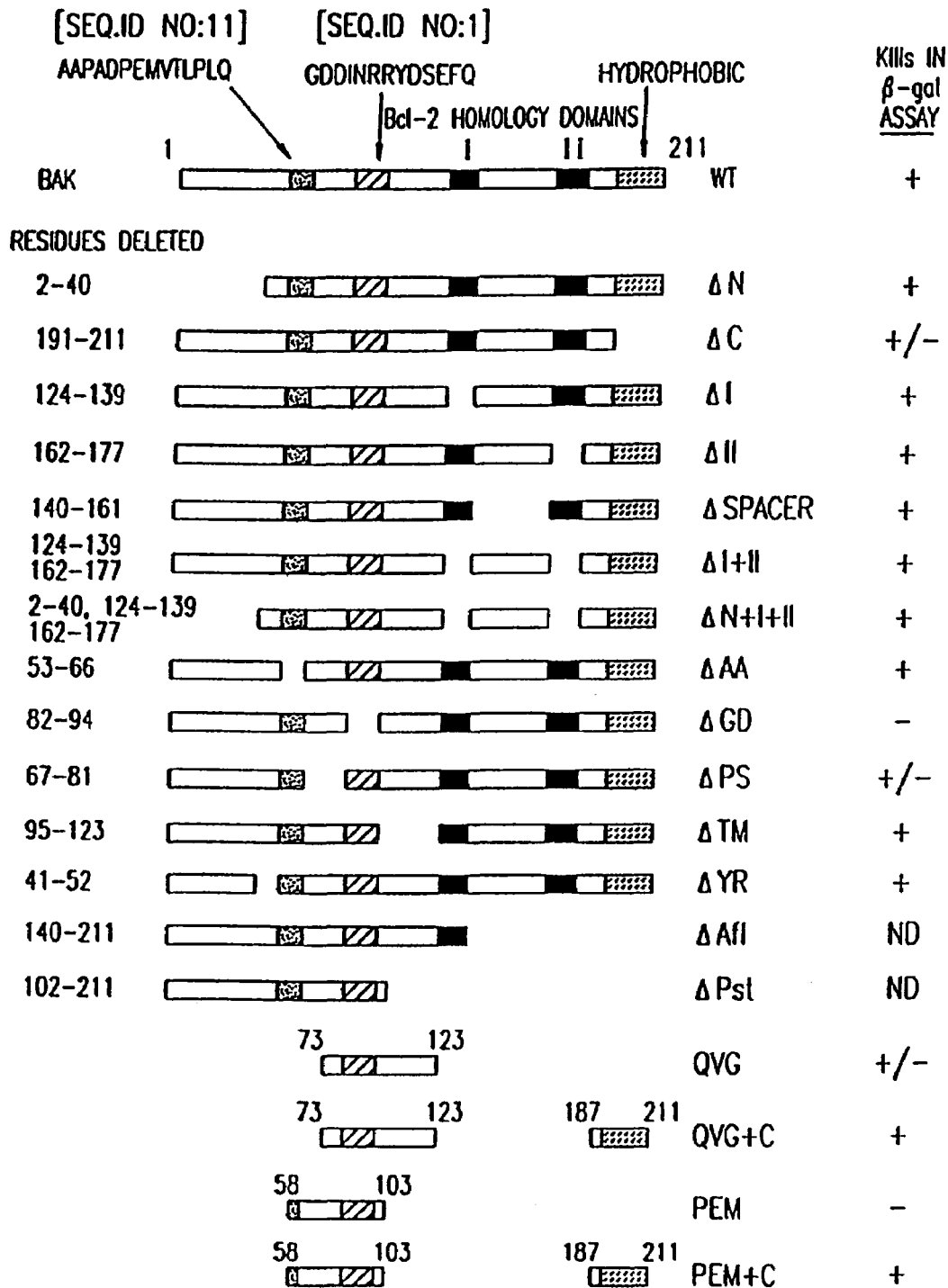

FIG. 2. Summary of the cell killing activity of Bak deletion mutants and truncated species.

The structures of the various Bak mutants are illustrated schematically. The precise amino acid region(s) removed by deletion are indicated by the numbers at the left [SEQ ID NOS: 11 and 1]. The endpoints of the Bak amino acid residues retained in the truncated species (bottom, QVG and PEM) are indicated by numbers bordering the schematics of their respective structures. The Rat-1 cell killing activity is summarized as follows: +, cell killing capacity equivalent to wild-type Bak; -, no cell killing activity; +/-, diminished cell killing activity relative to wild-type Bak. and indicates experiment not done.

Figure 3A:
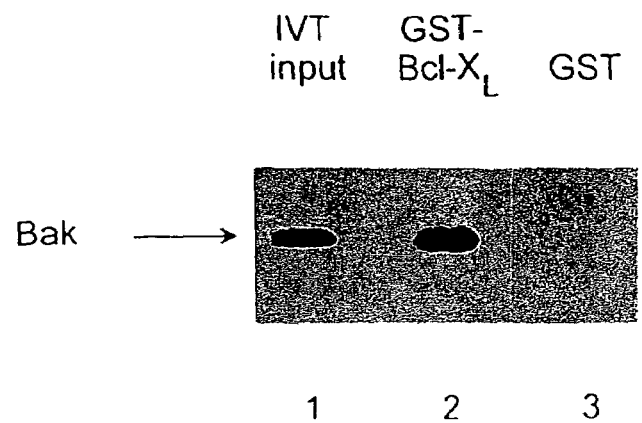
Figure 3B:
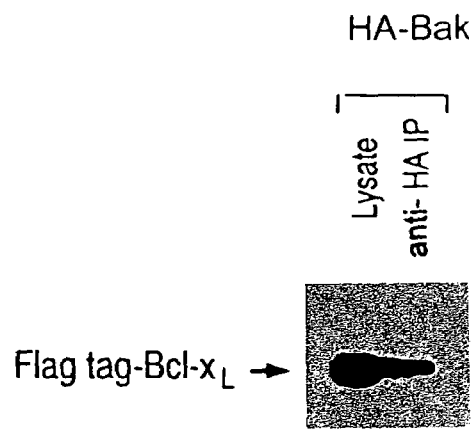

FIGS. 3A-B. Interaction of Bak with Bcl-$x_L$.

A). Bak/Bcl-xL interactions measured in vitro. $^{35}$S labeled in vitro translated Bak (lane 1) was mixed either with GST-Bcl-$x_L$ (lane 2) or GST (lane 3). The complexes were captured on glutathione-agarose beads, and bound $^{35}$S labeled Bak protein was detected by electrophoresis on SDS polyacrylamide gels followed by autoradiography.

B). Bak/Bcl-$x_L$ interactions detected in transfected cells. Plasmids expressing epitope-tagged forms of Bak and Bcl-$x_L$ (HA-Bak and Flag tag-Bcl-$x_L$) were co-transfected into COS cells. HA-Bak was immunoprecipitated (anti-HA IP) from transfected cell lysates and associated Bcl-$x_L$ was detected by Western blot analysis with an anti-Flag tag antibody.

Figure 4:
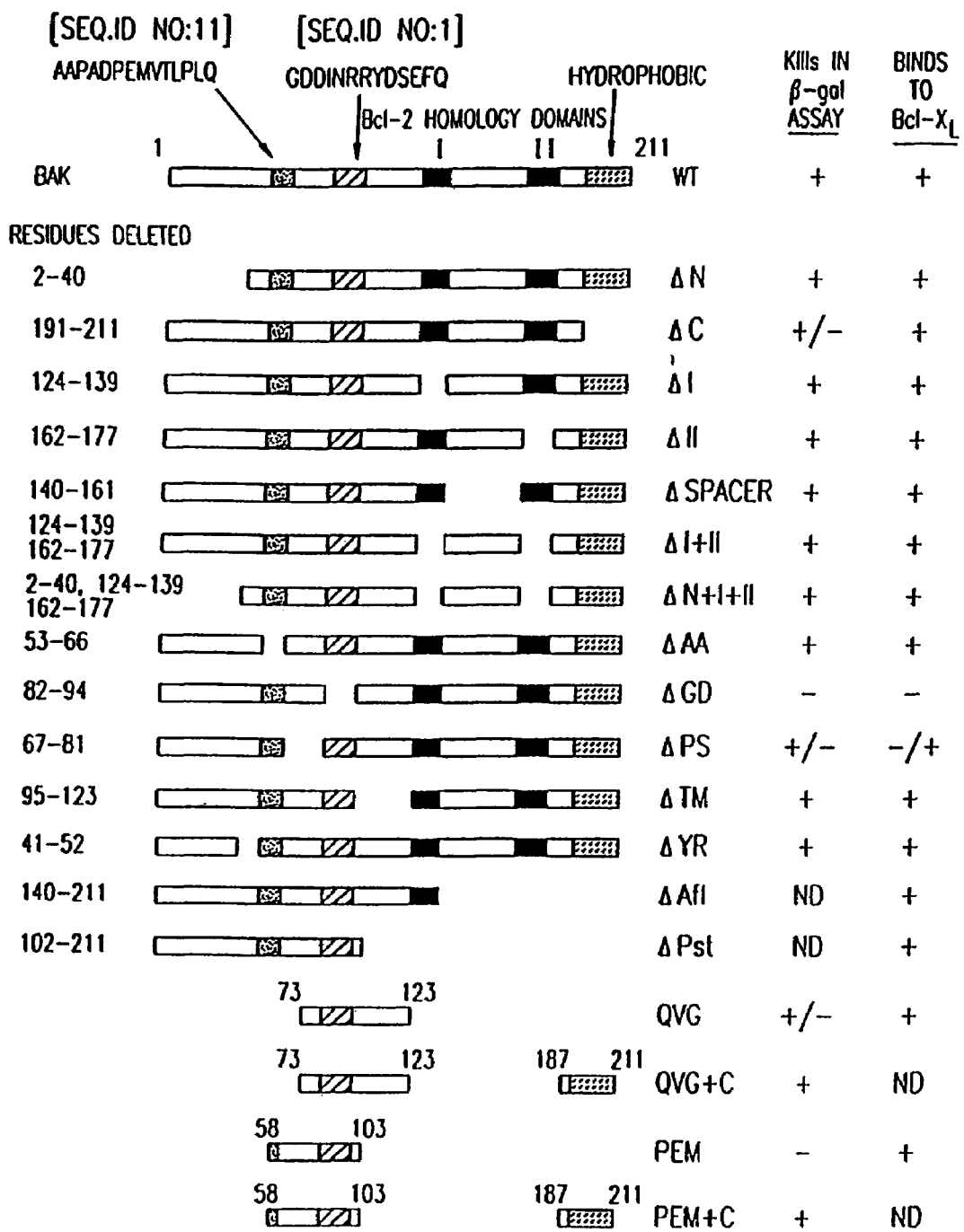

FIG. 4. Summary of Bcl-$x_L$ binding function of Bak deletions and truncated species.

The structures of the various Bak mutants are shown schematically, as described in FIG. 2 [SEQ ID NOs: 11 and 1]. The capacity of the Bak mutants and truncated species to interact with Bcl-$x_L$ is summarized (right) as follows: +, equivalent to wild type Bak in ability to interact with Bcl-$x_L$ both in vitro and in transfected COS cells; -, no interaction with Bcl-$x_L$ detected; -/+, interaction greatly diminished relative to wild-type Bak and could only be detected in vitro.

Figure 5:
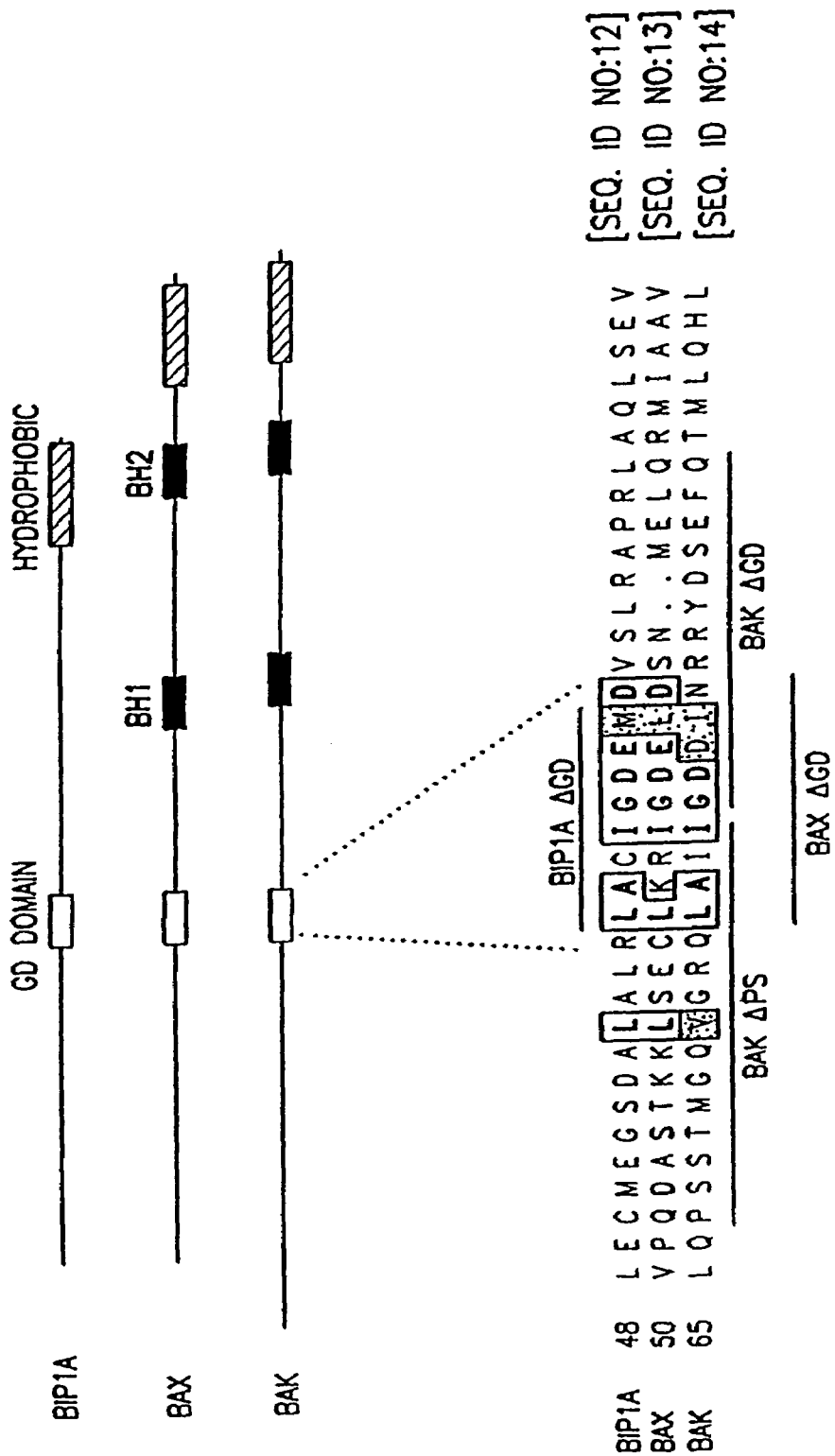

FIG. 5. Regions homologous to the Bak GD domain are present in Bip1a and Bax.

Top. Schematic structures of the proteins with the positions of the GD domain homology (open boxes), hydrophobic segment (hatched boxes) and Bcl-2 homology domains (filled boxes).

Bottom. Amino acid sequence of the regions in Bip1a [SEQ ID NO: 12] and Bax [SEQ ID NO: 13] homologous to the Bak GD domain [SEQ ID NO: 14]. Highlighted residues are identical in at least two of the proteins; shaded residues indicate conservative amino acid changes. Also shown (solid lines) are the amino acid regions removed in the indicated Bip1a, Bak and Bax deletion mutants.

FIG. 6. Summary of cell killing and Bcl-$x_L$ binding activities of GD domain deletion mutants.

The data for cell killing and Bcl-$x_L$ binding function are summarized as described in FIG. 2 and FIG. 4, respectively.

Figure 7:
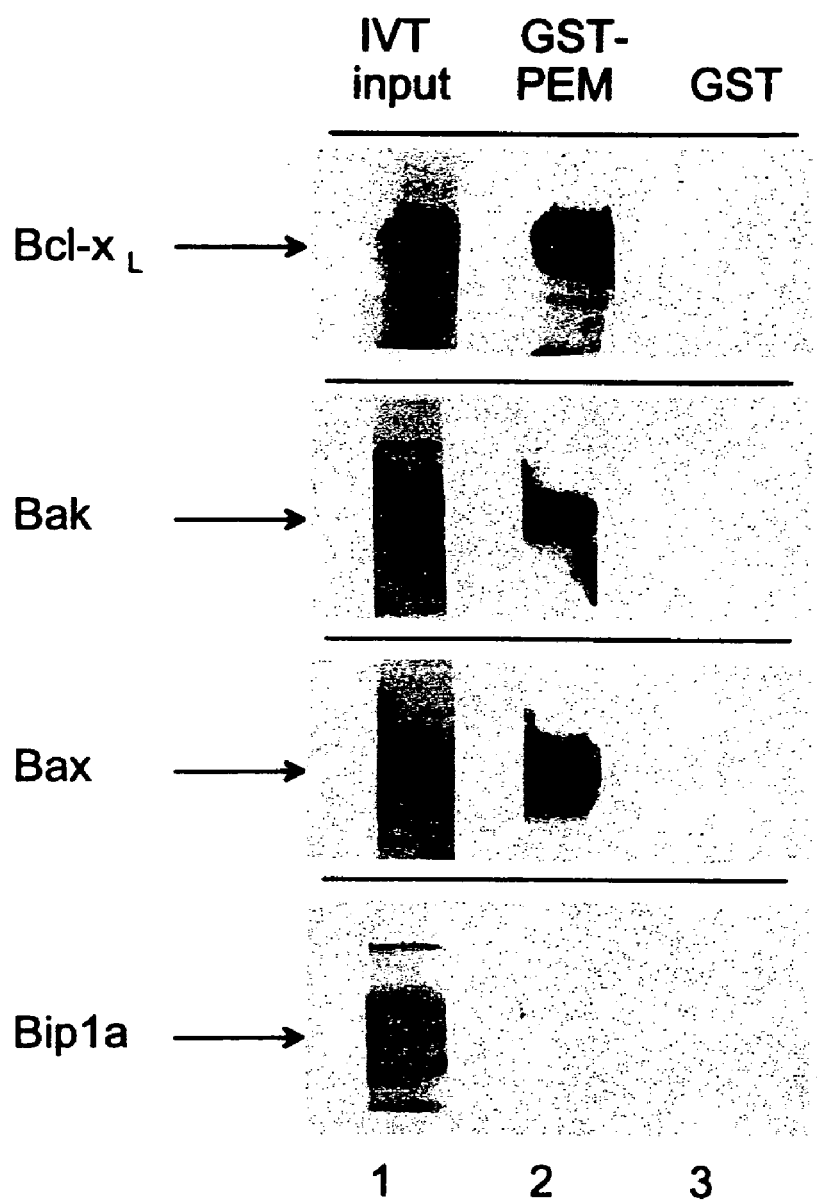

FIG. 7. Bak GD domain dimerization.

Interactions of the Bak GD domain with Bak and Bax were measured essentially as described for Bak binding to Bcl-$x_L$. A portion of Bak (PEM) encompassing the GD domain (residues 58-103) was fused to GST, to create GST-PEM. In vitro translated, $^{35}$S labeled Bcl-$x_L$, Bak, Bax and Bip1a were incubated with either GST alone, or GST-PEM bacterially-expressed fusion proteins. Complexes were captured with glutathione-agarose beads, washed, and bound proteins detected by polyacrylamide gel electrophoresis and autoradiography. Bcl-$x_L$, Bak, and Bax all interact specifically with GST-PEM, but not GST alone. Thus, the GD domain can mediate interaction not only with Bcl-$x_L$ but also Bak and Bax.

FIGS. 8A-8C. DNA sequences encoding the GD domain in Bak, Bax and Bip1a. A-C. DNA sequences encoding the GD domain regions for Bak (numbered 1-4 on the left; [SEQ ID NOs: 15, 17, 19 and 21]), Bax (numbered 5-7 on the left; [SEQ ID NOs: 23, 25 and 27]) and Bip1a (numbered 8-10 on the left; [SEQ ID NOs: 29, 31 and 33]) are shown along with their corresponding amino acid sequences [SEQ ID NOs: 3, 2, 10, 1, 6, 4, 5, 9, 7 and 8]. The nucleotide numbers above each sequence are based on starting at the initiating ATG for each protein. The underlined number refers to the position of the first and last amino acid of the peptide shown.

Figure 9:
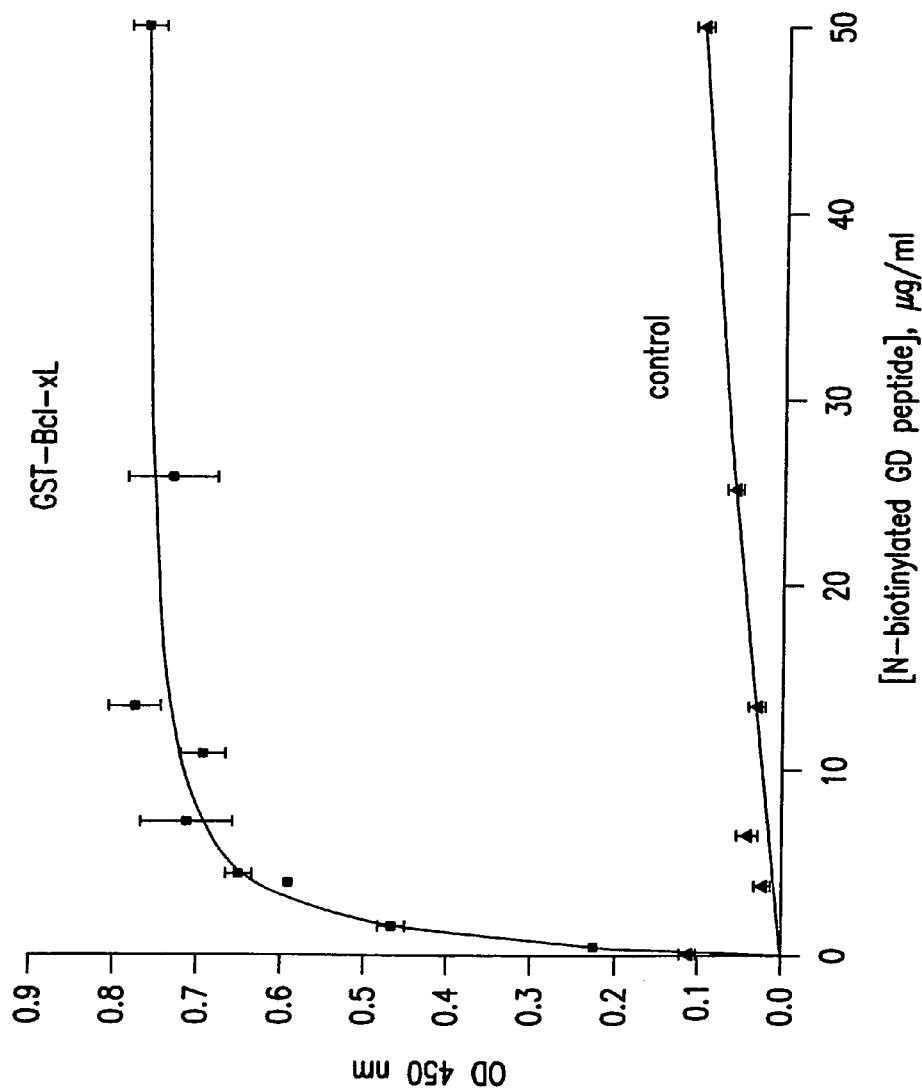

FIG. 9. High throuphput screening assay for agents that modulate GD domain binding with GST-Bcl-$x_L$-coated multiwell plates.

Multiwell plates (Nunc Maxisorp) were coated with GST-Bcl-$x_L$ and blocked with 1% normal goat serum in PBS. A N-biotinylated GD peptide corresponding to Bak (71-89; MGQVGRQLAIIGDDINRRY [SEQ ID NO: 35]) was added and the plates were incubated at 4° C. for 1 hour. The plates were washed to remove unbound GD peptide and the amount of bound peptide was determined by ELISA using streptavidin-conjugated horse radish peroxidase. Coating with GST-Bcl-$x_L$ was omitted in the control wells.

Figure 10:
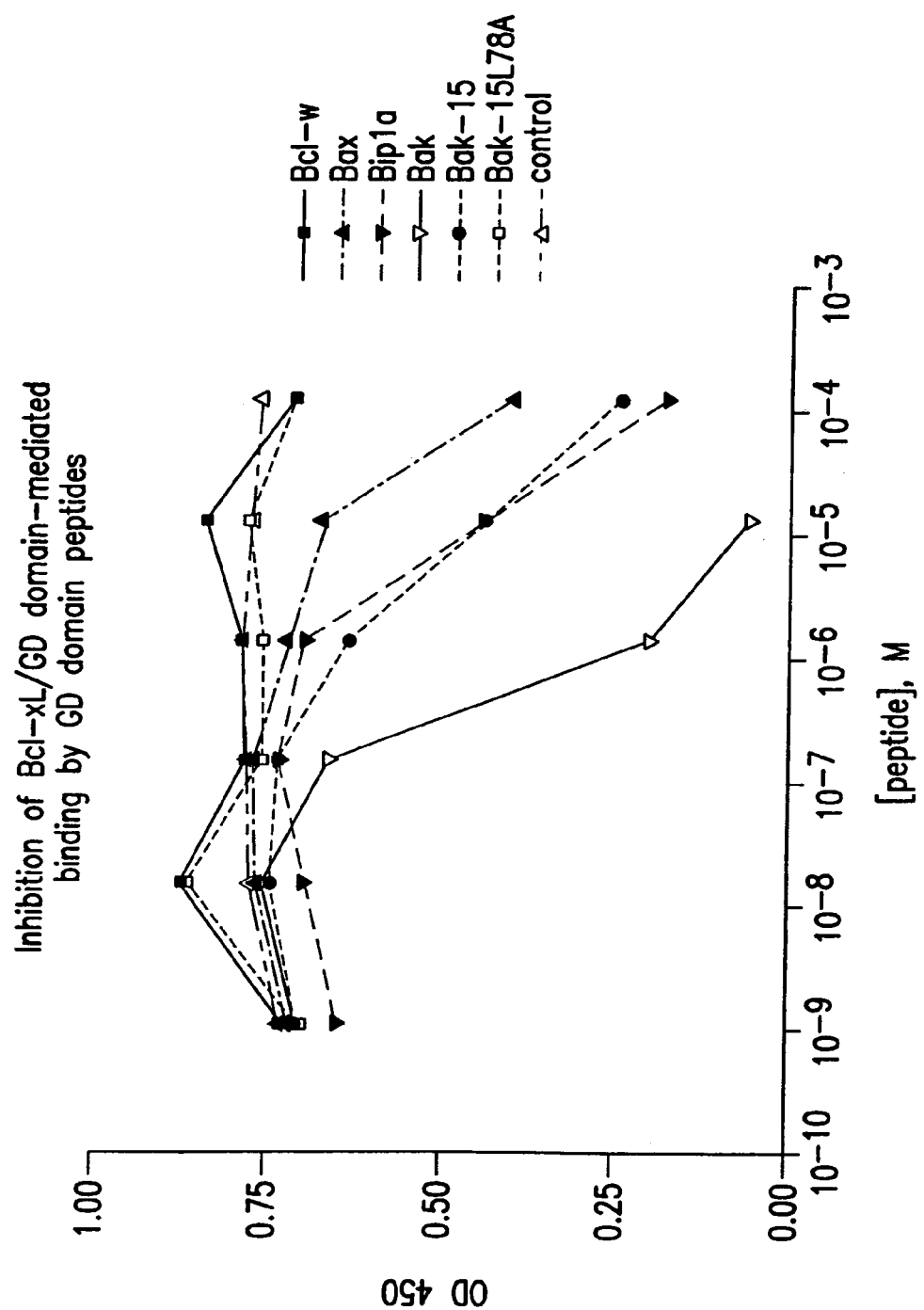

FIG. 10. High throughput screening assay for agents that modulate GD domain binding with GD domain peptide-coated multiwell plates.

An assay was developed to screen for compounds that block the interaction between the Bcl-2 homologs, Bcl-$x_L$ and Bak. A synthetic peptide corresponding to the Bak GD binding domain (MGQVGRQLAIIGDDINRRY [SEQ ID NO: 35]) was biotinylated and bound to wells coated with neutravidin. A GST-Bcl-$x_L$ fusion protein was shown to bind specifically to the GD peptide and the extent of binding was determined by ELISA using an anit-GST antibody conjugated with horse radish peroxidase. Peptides encompassing the GD domain from various Bcl-2 family members were tested for their ability to block GD domain-mediated interactions in this assay. Peptides tested: Bcl-w [SEQ ID NO: 39] (AADPLHQAMRAAGDEFETRF), Bax [SEQ ID NO: 40]STKKLSECLKRIGDELDSNH), Bip1a [SEQ ID NO: 41] (GSDALALRLACIGDEMDVSL), Bak [SEQ ID NO: 36](TMGQVGRQLAIIGDDTNRRY), Bak-15 [SEQ ID NO: 37] (QVGRQLAIIGDDINR), Bak-15L78A [SEQ ID NO: 38] (QVGRQAAIIGDDINR), control (no peptide).

Figure 11:
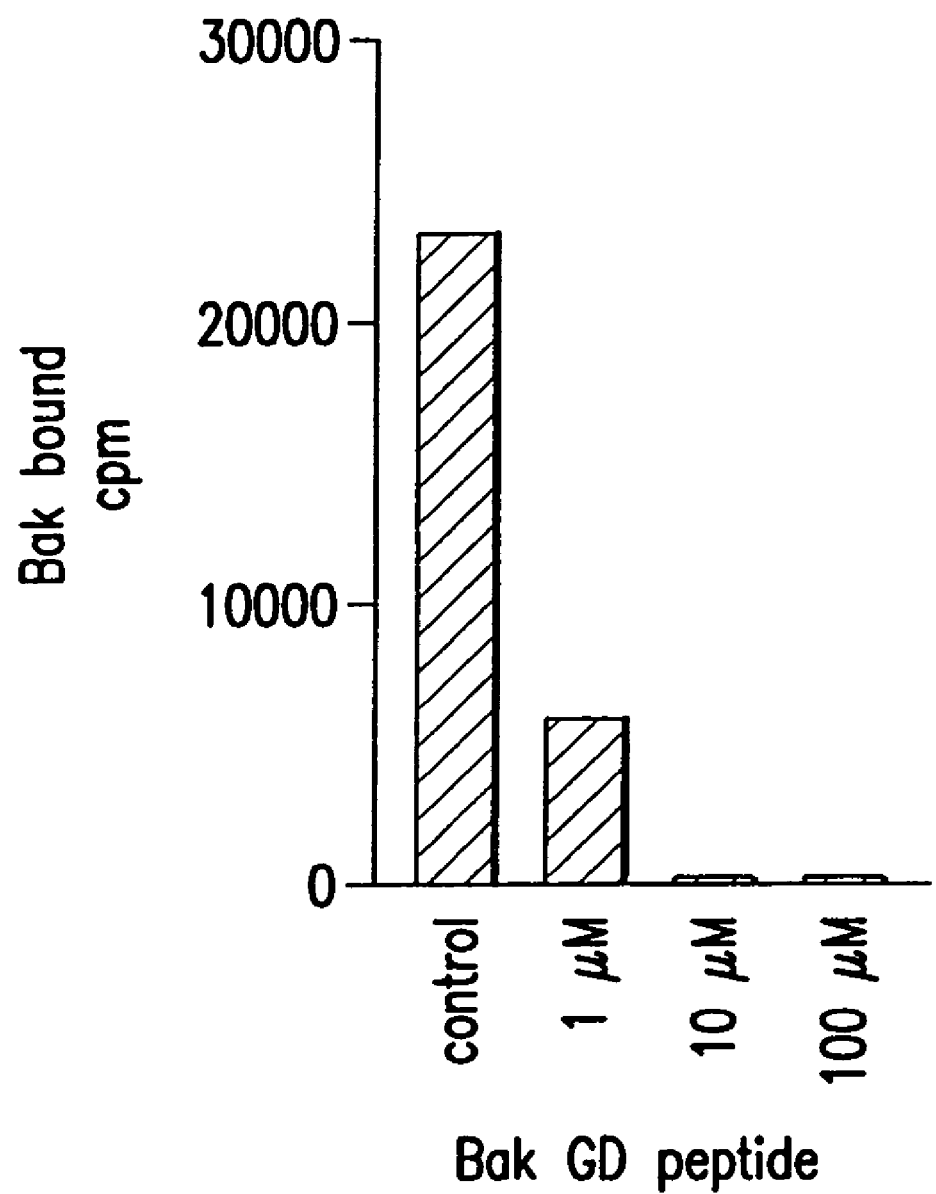

FIG. 11. Detection of a peptide that inhibits GD domain mediated protein/protein interactions using an in vitro binding assay.

An in vitro binding assay as described herein in Example A.3. was used to measure the inhibition of GST-Bcl-$x_L$ binding to in vitro translated $^{35}$Met-labeled Bak by a 20-amino acid peptide derived from the Bak GD domain (70-89; TMGQVGRQLAIIGDDINRRY [SEQ ID NO: 36]). The peptide was mixed with the GST-Bcl-$x_L$ protein 30 minutes prior to addition to the binding assay. The concentration of peptide in the binding assay is indicated. Control assay contains no peptide.

Figure 12:
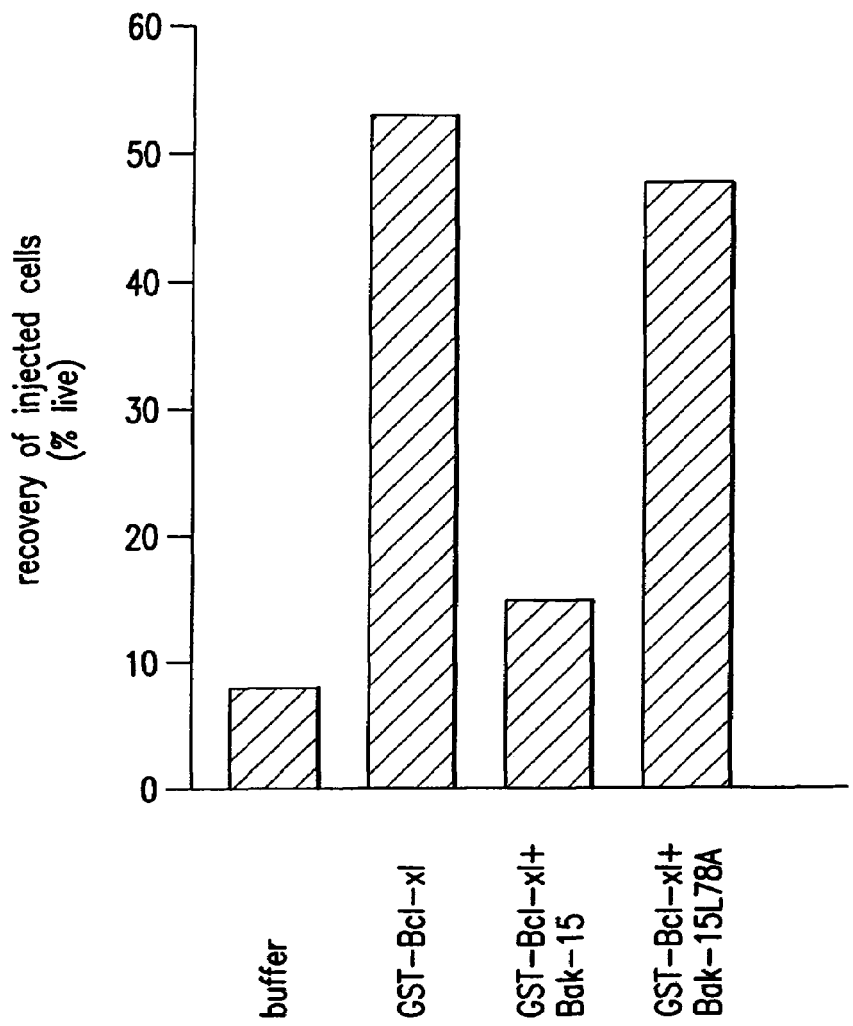

FIG. 12. Microinjection assay for agents that modulate GD domain binding and inhibit death suppressor activity.

HeLa cells (>100 cells/condition) were microinjected without (buffer) or with GST-Bcl-$x_L$ (0.3 mg/ml) in the absence or presence of GD domain peptides (0.5 mg/ml) and the recovery of live injected cells was determined after treatment with anti-Fas and cycloheximide for 18 hours. FITC-dextran was coinjected as a marker. A 15-amino acid Bak GD domain peptide (Bak-15; residues 73-87; QVGRQLAIIGDDINR [SEQ ID NO: 37]) and a mutant Bak GD domain peptide with an alanine substitution at leucine 78 (Bak-15L78A; QVGRQAAIIGDDINR [SEQ ID NO: 38]) were tested.

DETAILED DESCRIPTION OF THE INVENTION

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., *Molecular Cloning: A Laboratory Manual*, 2d Ed., Cold Spring Harbor Laboratory Press, Planview, N.Y. (1989); McPherson, M. J., Ed., *Directed Mutagenesis: A Practical Approach*, IRL Press, Oxford (1991); Jones, J., *Amino Acid and Peptide Synthesis*, Oxford Science Publications, Oxford (1992); Austen, B. M. and Westwood, O. M. R., *Protein Targeting and Secretion*, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

A previously unrecognized domain within the Bak molecule that appears to be both necessary and sufficient for the known biological activities of Bak has now been identified. This domain, designated herein as the "GD domain," is sufficient to mediate cell killing function and physical interaction with Bcl-$x_L$. Sequences homologous to the Bak GD domain have also been identified within Bax and Bip1a and shown to be similarly required for the cell killing and Bcl-$x_L$ binding activities of these proteins. These observations suggest that Bak, Bax and Bip1a modulate or regulate apoptosis through a similar mechanism that, in each case, involves their respective GD domains. As those of skill familiar with the present invention will appreciate, sequences comprising the GD domain are useful in modulating apoptosis in cells. Similarly, compounds and compositions which are capable of binding to the GD domain are useful as agents for the modulation of apoptotic activity in cells.

As used herein, the term "GD domain" refers to a protein domain first identified in Bak, demonstrated herein to be essential for the interaction of Bak with Bcl-xL and for Bak's cell killing function, and to peptides and/or molecules capable of mimicking its structure and/or function. In a preferred embodiment, the present invention comprises a peptide having the following amino acid sequence:

[SEQ ID NO:1]
GDDINRRYDSEFQ corresponding to amino acid residues 82-94 of Bak, as well as functional equivalents thereof. By "functional equivalent" is meant a peptide possessing a biological activity or immunological characteristic substantially similar to that of the GD domain, and is intended to include "fragments", "variants", "analogs", "homologs", or "chemical derivatives" possessing such activity or characteristic. Functional equivalents of the GD domain, then, may not share an identical amino acid sequence, and conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

In a preferred embodiment of the invention, there is provided a peptide having the following amino acid sequence:

[SEQ ID NO:2]
PSSTMGQVGRQLAIIGDDINRRYDSEFQ corresponding to amino acid residues 67-94 of Bak, uniquely required for Bak cell killing function.

In another preferred embodiment, there is provided a peptide having the following amino acid sequence:

[SEQ ID NO:3]
QVGRQLAIIGDDINRRYDSEFQTMLQHLQPT corresponding to amino acid residues 73-103 of Bak, sufficient for the cell killing function of Bak.

The present data indicate that the biological activity of the GD domain and its functional derivatives will be affected by the sub-cellular localization of these compositions. Accordingly, in another preferred embodiment of the invention, the GD domain peptides of the invention will have fused to their C-terminal end an appropriate hydrophobic tail, which may comprise amino acids 187-211 of Bak. Other suitable means of effecting sub-cellular localization, including the selection of suitable hydrophobic tails, such as amino acids 172-192 of Bax, amino acids 213-233 of Bcl-$x_L$, amino acids 220-240 of Bcl-2, and hydrophobic tails introduced through protein lipidation (Casey, T. J., *Science*, 268: 221-225 (1995)) such as prenylation and acylation (e.g., myristylation, palmitylation) may be employed by those of skill using known methods.

The GD domain disclosed herein is uniquely involved in both cell killing and Bcl-$x_L$ binding activity of Bak. Moreover, other Bcl-2 interacting proteins having functional properties resembling those of Bak are demonstrated herein to contain amino acid regions having sequences bearing homology to sequences within the GD domain of Bak. These proteins include Bax and Bip1a which, like Bak, interact with Bcl-2, and both of these proteins contain amino acid regions bearing homology to sequences within the GD domain of Bak. In Bax, this region comprises amino acids 59-73, which bears homology to amino acids 74-88 within the GD domain of Bak. The protein Bip1a similarly contains an amino acid region comprising amino acids 57-71 bearing homology to the same sequences (amino acids 74-88) within the Bak GD domain. Deletion of the Bax and Bip1a GD domain regions identified above impaired their cell killing activity and prevented binding to Bcl-$x_L$. Bip1a lacks sequences homologous to the two highly conserved regions, designated Domain I and Domain II (also referred to in the literature as "Bcl-2 Homology domains" or "BH domains" I and II or "BH1" and "BH2"). It has been suggested that these two conserved regions, and especially Domain I, are instrumental in dictating homo- and heterodimerization in Bcl-2, Bax, and other Bcl-2 family members. Accordingly, the GD domain constitutes a key element involved in the biological activity of proteins such as Bak, Bax and Bip1a, not necessarily shared with Bcl-2 family members, which activity is independent of BH domains I and II. This suggests that the GD domain defines a distinct family of proteins, including Bak, Bax and Bip1a.

Accordingly, in an additional preferred embodiment, there is provided a peptide comprising the following amino acids:

[SEQ ID NO:4]
LSECLKRIGDELDSN corresponding to amino acids 59-73 of Bax. In another preferred embodiment, a peptide is provided which comprises amino acid sequence:

[SEQ ID NO:5]
LKRIGDELD corresponding to amino acids 63-71 of Bax. In another preferred embodiment, a peptide is provided which comprises amino acid sequence:

[SEQ ID NO:6]
QDASTKKLSECLKRIGDELDSNMELQ corresponding to amino acids 52-77 of Bax. In another preferred embodiment, a peptide is provided which comprises amino acid sequence:

[SEQ ID NO:7]
LALRLACIGDEMDVS corresponding to amino acids 57-71 of Bip1a. In another preferred embodiment, there is provided a peptide comprising the following amino acid sequence:

[SEQ ID NO:8]
IGDEM corresponding to amino acids 64-68 of Bip1a. In another preferred embodiment, there is provided a peptide comprising the following amino acid sequence:

[SEQ ID NO:9]
CMEGSDALALRLACIGDEMDVSLRAPRL corresponding to amino acids 50-77 of Bip1a. In another preferred embodiment, there is provided a peptide comprising the following amino acid sequence:

[SEQ ID NO:10]
VGRQLAIIGDDINRR corresponding to amino acids 74-88 of Bak.

A surprising aspect of the present invention is the discovery that the GD domain alone is sufficient for homodimerization of Bak, as well as for heterodimerization of Bak with Bax and Bcl-$x_L$, and that the highly conserved Bcl-2 family Domains I and II are not necessary for this dimerization. This indicates that the GD domain is capable of modulating the function of proteins including Bak, Bax and Bcl-$x_L$ directly through dimerization, and thus may also modulate the function of other proteins including Bcl-2.

The functional importance of the GD domain, then, is likely to be related to its ability to mediate one or more protein/protein interactions with other Bcl-2 family members, or with other as yet unidentified cellular protein(s). It is possible that survival proteins like Bcl-2 and Bcl-$x_L$ suppress apoptosis by binding and inactivating proteins that actively promote cell death, such as Bak, Bax and Bip1a, through their GD domains. In support of this view, the interaction with Bax appears to be required for Bcl-2 to suppress apoptosis (Yin et al., *Nature* 369: 321-323 (1994)). A second possibility is that Bak, Bax, and Bip1a induce cell death by binding (via their GD domains) and inactivating proteins, including Bcl-2 and Bcl-$x_L$, that actively promote cell survival. It is also possible that Bak, Bax and Bip1a bind one or more additional cellular proteins and that this interaction mediates cell death function. The present inventor does not intend to be bound by a particular theory; however, regardless of its mechanism(s) of action, the GD domain in Bak, Bax and Bip1a is of central importance for mediating these protein/protein interactions.

Agents capable of modulating GD domain mediated protein/protein interactions may include peptides comprising the GD domain, as well as mutants of the GD domain or of proteins comprising the GD domain. A "mutant" as used herein refers to a peptide having an amino acid sequence which differs from that of the naturally occurring peptide or protein by at least one amino acid. Mutants may have the same biological and immunological activity as the naturally occurring GD domain peptide or the naturally occurring protein. However, the biological or immunological activity of mutants may differ or be lacking. For example, a GD domain mutant may lack the biological activity which characterizes naturally occurring GD domain peptide, but may be useful as an antigen for raising antibodies against the GD domain or for the detection or purification of antibodies against the GD domain, or as an agonist (competitive or non-competitive), antagonist, or partial agonist of the function of the naturally occurring GD domain peptide.

Modulation of GD domain mediated protein/protein interactions may be effected by agonists or antagonists of GD domain peptides as well. Screening of peptide libraries, compound libraries and other information banks to identify agonists or antagonists of the function of proteins comprising the GD domain is accomplished with assays for detecting the ability of potential agonists or antagonists to inhibit or augment GD domain binding, e.g., GD domain homodimerization or heterodimerization.

For example, high through-put screening assays may be used to identify compounds that modulate the protein binding function of the GD domain. Such screening assays facilitate the identification of compounds that accelerate or inhibit apoptosis by influencing protein/protein interactions mediated by the GD domain. For example, an in vitro screen for compounds that disrupt the Bak GD domain interaction with GST-Bcl-$x_L$ comprises multiwell plates coated with GST-Bcl-$x_L$ which are incubated with a labeled GD domain peptide probe in the presence of one or more compounds to be tested. Molecules that specifically disrupt the interaction could, in principle, bind to either the GD domain "ligand" or to the as yet undefined "receptor" domain in Bcl-$x_L$. Either class of compound would be a candidate apoptosis-modulating agent.

Thus, the invention provides a method of screening for an agent capable of modulating apoptosis which comprises coating a multiwell plate with GST-Bcl-$x_L$ and incubating the coated multiwell plate with a labeled GD domain peptide probe in the presence of an agent which it is desired to test, wherein disruption of GD domain interaction with GST-Bcl-$x_L$ indicates that said agent is capable of modulating apoptosis. Agents identified by this method are also contemplated embodiments of the invention.

Suitable labels include a detectable label such as an enzyme, radioactive isotope, fluorescent compound, chemiluminescent compound, or bioluminescent compound. Those of ordinary skill in the art will know of other suitable labels or will be able to ascertain such using routine experimentation. Furthermore, the binding of these labels to the peptides is accomplished using standard techniques known in the art.

A high speed screen for agents that bind directly to the GD domain may employ immobilized or "tagged" combinatorial libraries. Agents that bind specifically to such libraries are candidates to be tested for their capacity to block Bak/Bcl-$x_L$ interactions. As discussed above, such agents may function as suppressors of apoptosis by either directly inhibiting Bak (and/or Bax/Bip1a) function, or by increasing the effective activity of endogenous Bcl-2/Bcl-$x_L$ (or other Bcl-2 family member). Such agents would be useful for suppressing aberrant apoptosis in degenerative disorders or following ischemic injury.

Antibodies against the GD domain peptides of the invention may be used to screen cDNA expression libraries for identifying clones containing cDNA inserts encoding structurally related, immunocrossreactive proteins which may be members of the GD domain family of proteins. Screening of cDNA and mRNA expression libraries is known in the art. Similarly, antibodies against GD domain peptides are used to identify or purify immunocrossreactive proteins related to this domain, or to detect or determine the amount of proteins containing the GD domain in a cell or cell population, for example, in tissue or cells, such as lymphocytes, obtained from a patient. Known methods for such measurements include immunoprecipitation of cell extracts followed by PAGE, in situ detection by immunohistochemical methods, and ELISA methods, all of which are well known in the art.

Modulation of apoptosis according to the invention includes methods employing specific antisense polynucleotides complimentary to all or part of the nucleotide sequences encoding proteins comprising the GD domain disclosed herein. Such complimentary antisense polynucleotides may include nucleotide additions, deletions, substitutions and transpositions, providing that specific hybridization to the target sequence persists. Soluble antisense RNA or DNA oligonucleotides which can hybridize specifically to mRNA species encoding proteins comprising the GD domain, and which prevent transcription of the mRNA species and/or translation of the encoded polypeptide are contemplated as complimentary antisense polynucleotides according to the invention. Production of proteins comprising the GD domain is inhibited by antisense polynucleotides according to the invention, and such antisense polynucleotides may inhibit apoptosis, senescence and the like, and/or reverse the transformed phenotype of cells. A heterologous expression cassette maybe used to produce antisense polynucleotides in a transfectant or transgenic cell. Antisense polynucleotides also may be administered as soluble oligonucleotides to the external environment of the target cell, such as the culture medium of cells in vitro or the interstitial fluid (e.g., via the circulatory system) in vivo. Antisense polynucleotides and their use are known to those of skill, and are described, for example, in Melton, D. A., Ed, *Antisense RNA and DNA*, Cold Spring Harbor Laboratory Press, Cold Spring Harbor, N.Y. (1988).

The predicted biological activity of agents identified according to the invention varies depending on the assumptions made regarding the mechanism of Bak/Bcl-2 function. For example, an agent which binds tightly to the GD domain would be predicted to inhibit Bak (and perhaps Bax/Bip1a) function. Assuming Bak (and/or Bax/Bip1a) is the active cell death regulatory molecule, an agent that binds tightly to the GD domain may inhibit Bak function via a mechanism similar to the action of Bcl-2/Bcl-$x_L$ binding. Such agents would comprise "Bcl-2/Bcl-$x_L$" mimetics and might, therefore, exhibit anti-apoptotic activity under conditions in which Bcl-2 has a demonstrated protective effect (e.g., protection of neurons against injury or cytokine deprivation). Agents in this class could have utility in treating diseases characterized by excessive or inappropriate cell death, including, for example, neuro-degenerative diseases and injury resulting from ischemia.

If Bcl-2/Bcl-$x_L$ binding actively promotes cell survival, and if Bak repression is due simply to its binding and inactivating these survival proteins, then an agent that prevented this binding would effectively increase the activity of resident Bcl-2/Bcl-$x_L$ in a cell by relieving repression by Bak (and/or by Bax/Bip1a). This would also promote cell survival, but only in cells that express endogenous Bcl-2/Bcl-$x_L$. Agents that bind to Bcl-$x_L$ and thereby prevent its interaction with Bak (and/or with Bax/Bip1a) might inhibit the cell death suppression activity of Bcl-$x_L$ (and/or of Bcl-2). Such agents would comprise "GD domain mimetics" and would promote cell death in a fashion mechanistically similar to the action of Bak. GD domain mimetic agents would be useful in the therapeutic treatment of cancer and viral disease.

Peptidomimetics of GD domain peptide are also provided by the present invention, and can act as drugs for the modulation of apoptosis by, for example, blocking the function of proteins comprising the GD domain or interfering with GD domain mediated dimerization. Peptidomimetics are commonly understood in the pharmaceutical industry to include non-peptide drugs having properties analogous to those of those of the mimicked peptide. The principles and practices of peptidomimetic design are known in the art and are described, for example, in Fauchere J., *Adv. Drug Res.* 15: 29 (1986); and Evans et al., *J. Med. Chem.* 30: 1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage which may convert desirable properties such as resistance to chemical breakdown in vivo. Such linkages may include —$CH_2NH$—, —$CH_2S$—, —$CH_2$—$CH_2$—, —$CH=CH$—, —$COCH_2$—, —$CH(OH)CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

As discussed herein, the GD domain appears to be an area of motifs involved in dimerization, and this activity may be related to the regulation of apoptosis by proteins comprising the GD domain. Bak possesses a C-terminal hydrophobic region which appears to be membrane spanning. Thus, sub-cellular localization of proteins containing the GD domain may play a role in the regulation of programmed cell death in vivo. It is possible, then, to employ the invention for detection or determination of proteins comprising the GD domain, for example, in fractions from tissue/organ excisions, by means of immunochemical or other techniques in view of the antigenic properties thereof. Immunization of animals with peptides comprising the GD domain alone or in conjunction with adjuvants by known methods can produce antibodies specific for the GD domain peptide. Antiserum obtained by conventional procedures may be utilized for this purpose. For example, a mammal, such as a rabbit, may be immunized with a peptide comprising the GD domain, thereby inducing the formation of polyclonal antibodies thereagainst. Monoclonal antibodies also may be generated using known procedures. Such antibodies can be used according to the invention to detect the presence and amount of peptides comprising the GD domain.

The GD domain peptides of the invention may be used for the detection of Bak, Bcl-$x_L$, Bip1a and other proteins by means of standard assays including radioimmunoassays and enzyme immunoassays.

It will be appreciated by those of skill that the precise chemical structure of peptides comprising the GD domain will vary depending upon a number of factors. For example, a given protein may be obtained as an acidic or basic salt, or in neutral form, since ionizable carboxyl and amino groups are found in the molecule. For the purposes of the invention, then, any form of the peptides comprising the GD domain which retains the therapeutic or diagnostic activity of the naturally occurring peptide is intended to be within the scope of the present invention.

The GD domain peptides and other compositions of the present invention may be produced by recombinant DNA techniques known in the art. For example, nucleotide sequences encoding the GD domain peptides of the invention may be inserted into a suitable DNA vector, such as a plasmid, and the vector used to transform a suitable host. The recombinant GD peptide is produced in the host by expression. The transformed host may be a prokaryotic or eukaryotic cell. Preferred nucleotide sequences for this purpose encoding the GD domains of Bak, Bax and Bip1a are set forth in FIG. 8.

Polynucleotides encoding peptides comprising the GD domain may be genomic or cDNA, isolated from clone libraries by conventional methods including hybridization screening methods. Alternatively, synthetic polynucleotide sequences may be constructed by known chemical synthetic methods for the synthesis of oligonucleotides. Such synthetic methods are described, for example, in Blackburn, G. M. and Gait, M. J., Ed., *Nucleic Acids in Chemistry and Biology*, IRL Press, Oxford, England (1990), and it will be evident that commercially available oligonucleotide synthesizers also may be used according to the manufacturer's instructions. One such manufacturer is Applied Bio Systems.

Polymerase chain reaction (PCR) using primers based on the nucleotide sequence data disclosed herein may be used to amplify DNA fragments from mRNA pools, cDNA clone libraries or genomic DNA. PCR nucleotide amplification methods are known in the art and are described, for example, in Erlich, H. A., Ed., *PCR Technology: Principles and Applications for DNA Amplification*, Stockton Press, New York, N.Y. (1989); U.S. Pat. No. 4,683,202; 4,800,159; and 4,683,195. Various nucleotide deletions, additions and substitutions may be incorporated into the polynucleotides of the invention as will be recognized by those of skill, who will also recognize that variation in the nucleotide sequence encoding GD domain peptides may occur as a result of, for example, allelic polymorphisms, minor sequencing errors, and the like. The polynucleotides encoding GD domain peptides of the invention may include short oligonucleotides which are useful, for example, as hybridization probes and PCR primers. The polynucleotide sequences of the invention also may comprise a portion of a larger polynucleotide and, through polynucleotide linkage, they may be fused, in frame, with one or more polynucleotide sequences encoding different proteins. In this event, the expressed protein may comprise a fusion protein. Of course, the polynucleotide sequences of the invention may be used in the PCR method to detect the presence of mRNA encoding GD domain peptides in the diagnosis of disease or in forensic analysis.

cDNAs encoding proteins which interact with the GD domain (or proteins containing the GD domain) can be identified by screening cDNA expression libraries, employing known methods. Examples of such methods include the yeast two-hybrid system (U.S. Pat. No. 5,283,173, inventors Fields and Song, issued Feb. 1, 1994; Chien, et al., Proc. Natl. Acad. Sci. 88: 9578 (1991), and the *E. coli*/BCCP interactive screening system (Guarente, L., Proc. Natl. Acad. Sci. 90: 1639 (1993) and Germino, et al., Proc. Natl. Acad. Sci. 90: 933-937 (1993)). Suitable cDNA libraries will include mammalian cDNA libraries, such as human, mouse or rat, which may contain cDNA produced from RNA and a single cell, tissue or organ type or developmental stage, as are know in the art.

A nucleotide sequence encoding a protein or peptide comprising the GD domain may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, J., et al., *Molecular Cloning: A Laboratory Manual*, 2d Ed., Cold Spring Harbor Laboratory Press, Planview, N.Y. (1989), and are well known in the art.

The sequence of amino acid residues in a protein or peptide comprising the GD domain is designated herein either through the use of their commonly employed three-letter designations or by their single-letter designations. A listing of these three-letter and one-letter designations may be found in textbooks such as *Biochemistry*, Second Edition, Lehninger, A., Worth Publishers, New York, N.Y. (1975). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

The rational design of GD domain mimetics or binding molecules, based on modeled (or experimentally determined) peptide structure, may be carried out by those of skill, using known methods of rational drug design. Therapeutic or prophylactic methods for treating pathological conditions such as autoimmune disease, neurodegenerative disease, cancer and the like, are accomplished by the administration of an effective amount of a therapeutic agent capable of specifically inhibiting GD domain homodimerization or heterodimerization, thereby modulating the biological activity of GD domain containing proteins and the apoptotic state in a patient.

Truncated Bak molecules comprising the GD domain, such as QVG or PEM, as well as other small peptide derivatives that constitute a "minimal" GD domain, are demonstrated herein to retain the protein binding and cell killing function exhibited by wild-type Bak. These molecules, or peptidomimetic derivatives, may induce apoptosis in tumor cells by providing the same biological signal produced by high level expression of Bak (which has been shown to kill tumor cells in an in vitro assay). Such agents comprise a novel class of chemotherapeutic drug that would be predicted to operate independently of p53 status.

If interaction with Bak results in the suppression of the anti-apoptotic function of Bcl-$x_L$ and/or other Bcl-2 family members, then GD domain peptides, or agents that mimic the GD domain structure, may act as inhibitors of the anti-apoptotic function of proteins like Bcl-2. High level Bcl-2 expression has been implicated in the resistance of tumor cells to a variety chemotherapy drugs (Fisher et al., *Cancer Res,*. 53: 3321-3326 (1993); Miyashita and Reed, *Blood* 81: 151-157 (1993); Dole et al., *Cancer Res,*. 54: 3253-3259 (1994). Administration of GD domain mimetics may suppress Bcl-2 function and restore sensitivity of tumor cells to apoptosis induced by traditional chemotherapeutic agents. In addition, Bak or GD domain mimetics that inhibit Bcl-2 may themselves be selectively toxic to certain tumors, such as follicular lymphoma, that depend upon high level Bcl-2 activity for their continued growth and survival.

The GD domain mimetics of the invention may also have utility in combating viral infections. Apoptosis of infected cells, with associated DNA fragmentation, provides an important defense against viral pathogenesis by limiting viral titers and restricting viral propagation (Vaux et al., *Cell*, 76: 777-779 (1994). For this reason, viruses have evolved diverse mechanisms to suppress apoptosis of infected host cells. Certain viral proteins, such as Epstein-Barr virus BHRF-1, African Swine Fever Virus (ASFV) LHW5-HL, and Adenovirus E1B 19kD, appear to be structural or functional homologues of Bcl-2. A second Epstein-Barr virus gene, LMP1, transactivates the expression of the cellular bcl-2 gene in latently infected cells (Henderson et al., *Cell* 65: 1107-1115 (1991). In these cases, the apoptotic signal triggered by viral infection may be held in check by the action of a viral (or cellular) Bcl-2 homolog. A Bak GD domain mimetic that opposes the anti-apoptotic function of the viral/cellular Bcl-2 homolog would serve to alleviate this block and induce apoptosis in infected cells and consequently inhibit viral propagation. Anti-apoptotic proteins encoded by at least two unrelated viruses (EBV BHRF1 and Adenovirus E1B 19kD) have been demonstrated to interact with Bak. Experimental evidence supports the conclusion that disrupting the E1B 19kD/Bak interaction (i.e., by competing with a GD domain mimetic) would reduce viral titers and productive replication. Mutations in EIB 19kD that disrupt the interaction with Bak correspondingly abolish the anti-apoptotic function of E1B 19kD. Adenovirus strains encoding defective E1B 19kD proteins yield much lower progeny virus in vitro, due to apoptosis of infected cells (Pilder et al., *J. Virol.* 52: 664-671 (1984); Subramanian et al., *J. Biol. Chem.* 259: 11777-11783 (1984).

An additional mechanism whereby viruses impose a blockade on the apoptosis signal transduction pathway is through the inactivation of the p53 tumor suppressor-protein. Forced cellular proliferation caused by viral infection induces an apoptotic signal that requires p53 function (see e.g., Wu and Levine, *Proc. Natl. Acad. Sci. USA* 91: 3602-3606 (1994). Typically, p53 function is abrogated during infection by physical interaction with a viral gene product. Examples of viruses that encode p53 binding proteins include adenoviruses, polyoma viruses, papilloma viruses, and cytomegalovirus (Levine et al., *Nature* 351: 453-456 (1991); Speir et al., *Science* 265: 391-394 (1994). Infected cells are "primed" to undergo apoptosis,' but cell death is prevented or delayed by viral inhibition of p53 function. It is possible that this blockade in the apoptosis signal transduction pathway could be relieved, or bypassed, by an agent that modulates apoptosis downstream of p53. Bak, or GD domain mimetics, induce apoptosis independently of p53, and consequently provide a way to implement or restore the cell death signal that is suppressed in infected cells.

Any mode of administration which results in the delivery of the therapeutic agent across the cell membrane and into the desired cell is contemplated as within the scope of the present invention. The site of administration and cells will be selected by one of ordinary skill in the art based upon an understanding of the particular disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc., with the requirement that the therapeutic agent cross the cell membrane. Principles of pharmaceutical dosage and drug delivery are known and are described, for example, in Ansel, H. C. and Popovich, N. G., *Pharmaceutical Dosage Forms and Drug Delivery Systems*, 5th Edition, Lea & Febiger, Publisher, Philadelphia, Pa. (1990). It is possible, for example, to utilize liposomes to specifically deliver the agents of the invention. Such liposomes can be produced so that they contain additional bioactive compounds and the like such as drugs, radioisotopes, antibodies, lectins and toxins, which would act at the target site.

Suitable agents for use according to the invention include GD domain peptides and mimetics, fragments, functional equivalents and/or hybrids or mutants thereof, as well as vectors containing cDNA encoding any of the foregoing. Agents can be administered alone or in combination with and/or concurrently with other suitable drugs and/or courses of therapy.

The agents of the present invention are suitable for the treatment of degenerative disorders, including disorders characterized by inappropriate cell proliferation or inappropriate cell death or in some cases, both. Inappropriate cell proliferation will include the statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells. Inappropriate cell death will include a statistically significant decrease in cell number as compared to the presence of that particular cell type in the normal population. Such underrepresentation may be due to a particular degenerative disorder, including, for example, AIDS (HIV), which results in the inappropriate death of T-cells, and autoimmune diseases which are characterized by inappropriate cell death. Autoimmune diseases are disorders caused by an immune response directed against self antigens. Such diseases are characterized by the presence of circulating autoantibodies or cell-mediated immunity against autoantigens in conjunction with inflammatory lesions caused by immunologically competent cells or immune complexes in tissues containing the autoantigens. Such diseases include systemic lupus erythematosus (SLE), rheumatoid arthritis.

Standard reference works setting forth the general principles of immunology include Stites, D. P., and Terr, A. I., *Basic and Clinical Immunology*, 7th Ed., Appleton & Lange, Publisher, Norwalk, Conn. (1991); and Abbas, A. K., et al., *Cellular and Molecular Immunology*, W. B. Saunders Co., Publisher, Philadelphia, Pa. (1991).

The GD domain peptides, mimetics, agents and the like disclosed herein, as well as vectors comprising nucleotide sequences encoding them or their corresponding antisense sequences, and hosts comprising such vectors, may be used in the manufacture of medicaments for the treatment of diseases.

Cells and non-human transgenic animals having one or more functionally impaired alleles encoding a protein comprising the GD domain may be generated using homologous targeting constructs from genomic clones of proteins comprising the GD domain. Methods for the production of homologous targeting constructs are known and described, for example, in Bradley, et al., *Bio/Technology* 10: 534 (1992); and Koh, et al., Science, 256: 1210 (1992). For example, "knock-out" mice may be generated which are homozygous or heterozygous for an inactivated allele of a protein comprising the GD domain by use of homologous targeting. Such mice are useful as research subjects for the investigation of disease and for other uses. Methods of producing chimeric targeted mice are known and are described, for example, 'in Robertson, E. J., Ed., Teratocarcinomas and Embryonic Stem Cells: A Practical Approach, IRL Press, Washington, D.C. (1987), which also describes the manipulation of embryonic stem cells. In addition, transgenes, for expressing polypeptides comprising the GD domain at high levels or under the control of selected transcription control sequences may be constructed using the cDNA or genomic gene of a protein comprising the GD domain. Transgenes so constructed can be introduced into cells and transgenic non-human animals by known methods. Such transgenic cells and transgenic non-human animals may be used as screens for agents which modulate apoptosis.

The invention may be appreciated in certain aspects with reference to the following examples, offered by way of illustration, not by way of limitation.

EXAMPLES

A. Methods

1. Plasmids and DNA Manipulations.

All recombinant DNA procedures were performed by standard methods. Deletions in the bak cDNA were introduced by PCR mutagenesis, and truncated Bak species were constructed by PCR (White, B. A., Ed., "PCR Protocols: Current Methods and Applications," in, *Methods in Molecular Biology*, Humana Press, Totowa, Conn. (1993). The mutations were confirmed by DNA sequence analysis. All Bak derivatives were tagged at the amino-terminus with influenza virus hemagglutinin epitope, and expressed from the CMV enhancer promoter present in pcDNA-1/Amp, pRcCMV, and pcDNA-3 (Invitrogen, Inc.).

2. Transient Transfection Assay.

The transient transfection assay procedure is similar to that previously described for detecting apoptosis induced by IL-1E-converting enzyme (Miura et al., *Cell* 75: 653-660 (1993); Kumar et al., *Genes Dev.* 8: 1613-1626 (1994); Wang et al., Cell 78: 739-750 (1994). One day prior to transfection, Rat-1 cells were plated in 24 well dishes at $3.5 \times 10^4$ cells/well. The following day, the cells were transfected with a marker plasmid encoding β-galactosidase (0.16 μg), in combination with an expression plasmid encoding Bak (0.42 μg), by the Lipofectamine procedure (Gibco/BRL). At 24 hours post transfection, cells were fixed and stained with X-Gal to detect J-galactosidase expression in cells that received plasmid DNA (Miura et al., supra). The number of blue cells was counted by microscopic examination and scored as either live (flat blue cells) or dead (round blue cells). The cell killing activity of Bak in this assay is manifested by a large reduction in the number of blue cells obtained relative to co-transfection of the β-gal plasmid with a control expression vector (i.e., with no bak cDNA insert).

The interpretation that loss of blue cells reflects the cell killing function of Bak is supported by a variety of observations:

1. Rat-1 cells are rapidly killed by enforced Bak expression in stable transfection assays;
2. Control expression plasmids harboring the bak cDNA in the anti-sense orientation, or various unrelated cDNAs, do not eliminate β-gal positive cells. In addition, certain Bak mutants (i.e., ΔGD) have greatly diminished capacity to eliminate blue cells in this assay;
3. IL-1 β-converting enzyme, previously shown to induce apoptosis in Rat-1 cells (Miura et al., supra; Kumar et al., supra; Wang et al., supra), also eliminates blue cells in this assay when expressed from the same vector;
4. The number of blue cells can be partially restored by co-transfection of Bak with Bcl-$x_L$. Thus, Bak expressing cells can be rescued to some degree by the anti-apoptotic function of Bcl-$x_L$, and Bak expression per se does not eliminate β-galactosidase activity.

3. Detection of Protein/Protein Interactions in Vitro.

GST and GST-Bcl-$x_L$ were expressed in *E. coli* and purified by affinity chromatography using glutathione-agarose (Smith and Johnson, Gene, 67 : 31-40 (1988)). $^{35}$S-Methionine-labeled proteins were expressed in vitro using a coupled transcription/translation system in rabbit reticulocyte lysates as described by the supplier (Promega). $^{35}$S-met-labeled proteins were precleared by mixing with 20 ml BSA-washed GSH-agarose beads (50% slurry) at 4° C. for 1 hour in 0.1 ml 10 mM Hepes buffer, pH 7.2 containing 0.25% NP-40, 142.5 mM NaCl, 5 mM MgCl$_2$, and 1 mM EGTA (NP-40 lysis buffer). The beads were removed by centrifugation and the supernatants were incubated with GST or GST-Bcl-$x_L$ (final concentration 1 mM) at 4° C. for 1 hour. The GST fusion proteins and any interacting proteins were recovered by incubation for 1 hour with an additional 20 ml of GSH-agarose beads. The beads were washed twice with NP-40 lysis buffer followed by two washes with NP-40 lysis buffer without NP-40. Proteins were eluted from the beads by incubation in SDS-PAGE sample buffer at 100° C. for 5 min and loaded onto 4-20% SDS-polyacrylamide gels. Following electrophoresis, gels were fixed and incubated in a fluorography enhancing solution (Amplify; Amersham). The gels were dried and subjected to autoradiography at −70° C.

4. Detection of Protein/Protein Interactions in Transfected Cells.

COS cells were grown in Dulbecco's modified Eagle's medium (Life Technologies, Inc.) supplemented with 10% bovine calf serum, 2% L-glutamine and 1% pen/strep (Life Technologies, Inc.). Cells were seeded at $2.0 \times 10^5$ cells/35 mm well and transfected with expression plasmids 24 hours later using Lipofectamine as described by the supplier (Life Technologies, Inc.). Bak (and Bak mutants) was expressed as a fusion protein with the HA epitope tag at its amino terminus. Bcl-$x_L$ was also expressed with an amino terminal epitope tag (Flag; Kodak). At 24 hours post-transfection, cells were washed with phosphate buffered saline and lysed in NP-40 Lysis buffer also containing 1 mM PMSF, 1 mM pepstatin, and 1 mg/ml leupeptin. The lysates were incubated with anti-HA antibody (12CA5, Boehringer Mannheim) for 1 hour and with 20 ml BSA-washed Protein A-agarose beads (50% slurry) for an additional hour. The beads were washed twice with NP-40 lysis buffer followed by two washes with NP-40 lysis buffer without NP-40. Proteins were eluted from the beads by incubation in SDS-PAGE sample buffer at 100° C. for 5 min and loaded onto 4-20% SDS-polyacrylamide gels. Following electrophoresis, proteins were transferred to Immobilon-P membranes (Millipore) and the membranes were blocked by incubation for 1 hour with a 1% milk solution in PBS. Primary antibody (1 mg/ml 12CA5, Boehringer Mannheim; 1:500 DAKO-bcl-2, 124, DAKO; 10 mg/ml Anti-FLAG M2, Kodak) was incubated with the membranes for 1 hour, followed by secondary antibody (0.8 mg/ml HRP-conjugated goat 5 anti-mouse IgG; Jackson Laboratory) for an additional 1 hour. Detection was by enhanced chemiluminesence (ECL; Amersham) as described by the supplier using X-OMAT AR film (Kodak).

B. Results

1. Detection of the Cell Death Function of Bak in Multiple Cell Lines.

Enforced bak expression induces apoptosis in stable Rat-1 cell lines transfected with an inducible bak expression plasmid. In order to more rapidly assess the cell killing function of a large number of bak mutants, a transient transfection assay was employed. Rat-1 cells were transfected with a marker plasmid encoding β-galactosidase, in combination with an expression plasmid encoding Bak, or various control plasmids. Cell killing activity of Bak in this assay was manifested by a large reduction in the number of blue (β-gal expressing) cells obtained relative to co-transfection of the β-gal plasmid with a control expression vector (FIG. 1).

The elimination of blue cells indicated that transfected cells were killed by bak prior to expressing detectable levels of β-galactosidase.

Bak cell killing activity was assessed in several additional cell lines. To determine whether Bak requires wild-type p53 to induce apoptosis, a transient transfection experiment was performed in transformed fibroblasts derived from a p53-/- "knockout" mouse. These cells lack functional p53 and are greatly impaired in their ability-to undergo apoptosis in response to g-irradiation and DNA-damaging chemotherapeutic drugs (Lowe et al., Cell 74: 957-967 (1993); Lowe et al., Nature, 362: 847-849 (1993)). Co-transfection of Bak with β-gal greatly reduced the number of blue cells (FIG. 1) indicating that Bak does not require wild-type p53 to exert its cell killing function. Similarly, transient transfection experiments performed in the Hela (cervical carcinoma) and BT549 (breast carcinoma) cell lines demonstrated that Bak can kill human tumor cells in this context (FIG. 1) indicating that its activity is not restricted to rodent fibroblasts.

2. Identification of Bak Domains Required for Cell Killing Function.

A mutational analysis of Bak was undertaken in order to identify regions of the molecule that are necessary and/or sufficient to induce apoptosis. A series of deletion mutations spanning the entire Bak protein was introduced by PCR mutagenesis and each mutant was tested for cell killing activity in a Rat-1 cell transient transfection assay. This analysis revealed that much of the Bak molecule is dispensable for its cell death function detected by this assay (FIG. 2). Surprisingly, the non-essential regions of the Bak protein include the two domains in the carboxyl terminal half of the protein that show the highest degree of homology to other Bcl-2 family members (Bcl-2 homology domains I and II).

Deletion of the carboxyl-terminal hydrophobic stretch of amino acids (residues 191-211) partially diminished, but did not eliminate, the cell killing function of Bak (mutant ΔC). This hydrophobic "tail" likely serves as a membrane anchor sequence in Bak. Indeed, immunofluorescence studies of ΔC in transiently transfected COS cells showed that the intracellular distribution of the ΔC mutant is altered (diffuse cytoplasmic) relative to the wild type Bak, which appears largely mitochondrial. The carboxyl terminal hydrophobic tail is not required for the cell killing function of Bak, but may contribute indirectly, by ensuring proper sub-cellular localization of the protein.

A segment of the Bak protein encompassed by the ΔGD deletion (residues 82-94) is absolutely required for cell death function since this mutant is devoid of cell killing activity in the transient transfection assay. Specifically, co-transfection of β-gal with Bak ΔGD yielded as many, or more, blue cells relative to co-transfection of β-gal with the control vector plasmid. Deletion of adjoining residues (amino acids 67-81) immediately N-terminal to this domain reduced, but did not eliminate, cell death activity (Bak mutant ΔPS). All other deletion mutants tested (with the exception of ΔC, discussed above) were unaltered in their capacity to kill cells. Taken together, these results indicate that a co-linear segment (termed the "GD domain") defined by deletion mutants ΔGD and ΔPS (residues 67-94) is uniquely required for Bak cell killing function detected in the transient assay.

To determine if the GD domain is sufficient for cell killing function, two truncated Bak protein derivatives, PEM and QVG, corresponding to amino acids 58-103 and 73-123, respectively, were tested for activity in the transient transfection assay. QVG significantly reduced the number of blue cells when co-transfected with β-gal, indicating that it retained some capacity to kill Rat-1 cells. While the reduction in blue cell number was diminished relative to full length Bak, both PEM and QVG lack the carboxyl-terminal membrane anchor and, by analogy to the Bak ΔDC mutant, would likely not exhibit full cell killing function due to altered sub-cellular localization. Indeed, QVG was similar to the Bak ΔC mutant with respect to its activity. In an effort to improve the cell killing capacity of the truncated Bak species, the hydrophobic tail element (amino acids 187-211) was fused to the C-termini of both PEM and QVG (PEM+C and QVG+C, respectively). In each case, attachment of the putative membrane anchor improved the ability of the truncated Bak mutants to eliminate blue cells in the transfection assay, and resulted in activity comparable to wild-type Bak (FIG. 2). Thus, these results indicate that a protein domain shared by both PEM and QVG (residues 73-103) is sufficient for the cell killing function of Bak.

3. Identification of Bak Domains that Mediate the Interaction with Bcl-$x_L$

Physical interaction with other Bcl-2 family members, such as Bcl-$x_L$, may be essential for Bak to exert its cell death function or may regulate Bak activity. Therefore, domains within Bak were examined to determine which are necessary and/or sufficient for its Bcl-$x_L$ binding activity. The interaction of Bak with Bcl-$x_L$ was measured both by an in vitro protein binding assay and by co-immunoprecipitation from transfected cells. In vitro translated $^{35}$S labeled Bak binds to a purified, bacterially expressed GST-Bcl-x, fusion protein, and the specificity of this in vitro interaction was demonstrated by the failure of Bak to bind to purified GST alone (FIG. 3A). A specific Bak/Bcl-$x_L$ interaction could also be detected by co-transfecting epitope tagged forms of Bak and Bcl-$x_L$ into COS cells. Bak was immunoprecipitated from transfected cell lysates and associated Bcl-$x_L$ was detected by western blot analysis of co-precipitated proteins (FIG. 3B). Bcl-$x_L$ was not detected in immunoprecipitates in the absence of co-expressed Bak, demonstrating that binding is specific.

The Bak deletion mutants described above were tested for their Bcl-x binding capacity, both in vitro and in transfected COS cells, and the results are summarized in FIG. 4. Deletion of residues 82-94 (ΔGD mutant) completely eliminated the ability of Bak to interact with Bcl-$x_L$. Interaction with Bcl-$x_L$ was also diminished by deletion of adjoining amino acids 67-81 (ΔPS Bak mutant). All other deletion mutants tested, encompassing the entire Bak open reading frame, retained the ability to bind Bcl-$x_L$ in these assays. These results identify Bak sequences encompassed by the ΔGD and ΔPS mutants (maximally, amino acids 67-94) as uniquely important in mediating the interaction with BCl-$x_L$. The same Bak region, the GD domain, was required for the cell killing function of Bak.

To determine whether the Bak region defined by deletion analysis is sufficient for protein binding function, two small truncated Bak species (PEM and QVG), encompassing amino acids 58-103 and 73-123 respectively, were tested for their ability to interact with Bcl-$x_L$. Both PEM and QVG bound Bcl-$x_L$, indicating that the region shared by both of these truncated Bak species (amino acids 73-103) was sufficient for mediating the interaction with Bcl-$x_L$. Together with the analysis of the deletion mutants and truncated species described above, these results demonstrate that Bak amino acid sequences spanning residues 73-103 are both necessary and sufficient for interaction with Bcl-$x_L$. As described above, this region is also implicated in the cell killing function of Bak, indicating that protein binding function may linked to cell killing function.

4. Functionally Significant Sequence Elements Resembling the GD Domain are Present in Bax and Bip1a.

The mutational analysis of Bak described herein demonstrates that the GD domain is uniquely involved in both the cell killing and Bcl-$x_L$ binding activities of Bak. Two other Bcl-2 interacting proteins, Bax and Bip1a, have functional properties that resemble those of Bak. Both Bax and Bip1a eliminate blue cells when co-transfected with β-gal in Rat-1 cells, indicating that they also induce apoptosis in this context. Bax and Bip1a also interact specifically with Bcl-$x_L$, both in vitro and in transfected COS cells. These functional similarities prompted the examination of whether any structural features are shared by the three proteins that contribute to their similar biological functions. Specifically, in light of the analysis presented above, Bax and Bip1a were examined to determine whether they contain sequences that resemble the Bak GD domain and are also important for their biological activities.

Bax shows extensive homology to Bcl-2 family members (including Bak), with the highest degree of sequence homology centered around BH1 and BH2 (Oltvai et al., Cell 74: 609-619 (1993)). A stretch of amino acids (59-73) N-terminal to BH1 in Bax bears homology to sequences (residues 74-88) within the GD domain of Bak (FIG. 5). In contrast to Bax., the primary sequence of Bip1a does not resemble the known Bcl-2 relatives, and lacks sequences homologous to BH1 and BH2 that are characteristic of the Bcl-2 family. However, Bip1a contains a region (amino acids 57-71) that is homologous to the same element within the GD domain in Bak and Bax (FIG. 5).

GD domain elements within Bax and Bip1a were evaluated to determine whether they are also critical to the cell killing and protein binding functions of these proteins. Small deletions that removed the conserved GD domain motifs were introduced into Bax and Bip1a, and the mutants were then analyzed for their ability to kill Rat-i cells and bind to Bcl-$x_L$. This analysis revealed that, like Bak ΔGD, the Bax ΔGD and Bip1a ΔGD mutants are impaired in their ability to eliminate blue cells when co-transfected with β-gal in Rat-1 cells (FIG. 6). In addition, both mutants no longer have the capacity to interact with Bcl-$x_L$ (FIG. 6). Thus, function of the GD domain element is conserved in Bak, Bax and Bip1a, and is critical to the biological activities of all three proteins.

5. The GD Domain is Sufficient for Homo- and Heterodimer Formation.

In order to assess whether the GD domain mediates other protein/protein interactions which could be relevant to its biological activity, a portion of Bak (PEM) encompassing the GD domain (residues 58-103) was fused to GST, to create GST-PEM. In vitro translated, $^{35}S$ labeled Bcl-$x_L$, Bak, Bax and Bip1a were incubated with either GST alone, or GST-PEM bacterially-expressed fusion protein. Interactions of the GD domain with Bak and Bax were measured essentially as described herein for Bak binding to Bcl-$x_L$. Complexes were captured with glutathione-agarose beads, washed, and bound proteins detected by polyacrylamide gel electrophoresis and autoradiography.

The results of this experiment are shown in FIG. 7. Bcl-$x_L$, Bak, and Bax all interact specifically with GST-PEM, but not with GST alone. These results demonstrate that the Bak GD domain is sufficient to bind to Bak (homodimerization), Bax (heterodimerization with a different killer protein) and Bcl-$x_L$ (heterodimerization with a survival protein). Thus, the GD domain is capable of mediating interactions not only with Bcl-$x_L$, but also Bak and Bax. It does not interact with Bip1a.

C. High Through-Put Screening Assays Using GD Domain Peptide Variants

To illustrate presently preferred embodiments of the invention for the identification of useful compounds, compositions and agents employing GD domain variants as described herein, a high through-put screening assay as described herein was carried out using exemplary and presently preferred variants of the GD domain peptide PSSTMGQVGRQLAIIGDDINRRYDSEFQ (amino acid residues 67-94; [SEQ ID NO: 2]) derived from Bak, and lacking the first four and last five amino acids (amino acid residues 71-89; MGQVGRQLAIIGDDINRRY [SEQ ID NO: 35]), or lacking the first three and last five amino acids (amino acid residues 70-89; TMGQVGRQLAIIGDDINRRY; [SEQ ID NO: 36]).

1. High Through-Put Screening Assay 1

According to the present example, multiwell plates coated with GST-Bcl-$x_L$ were incubated with a labeled GD domain peptide probe. The results shown in FIG. 9 demonstrate the feasibility of this assay approach. More specifically, wells in a multiwell plate were coated without (control) or with GST-Bcl-$x_L$ and then incubated with a GD domain peptide derived from the Bcl-2 homolog Bak (amino acid residues 71-89; MGQVGRQLAIIGDDINRRY [SEQ ID NO: 35]). The peptide was labeled by biotinylation at the amino terminus to allow detection and quantitation of bound peptide using streptavidin-conjugated horse radish peroxidase (HRP) in a standard ELISA procedure. The results show that the GD domain peptide specifically interacts in a concentration-dependent manner with the GST-Bcl-$x_L$-coated wells. Compounds that antagonize GD domain-mediated interactions can be conveniently identified using this assay by adding candidate compounds to the wells during the binding step. Those compounds that disrupt the interaction of the biotinylated GD domain peptide with GST-Bcl-$x_L$ will cause a decrease in the ELISA signal.

2. High Through-Put Screening Assay 2

In a modification of the high through-put screening assay 1 described herein, wells are coated with an avidin derivative, to which a biotinylated peptide/protein is bound. A GST-fusion protein that can interact with the biotinylated peptide/protein is added in the presence or absence of test compounds. The plates are incubated and then unbound GST-fusion protein is removed by washing. The amount of GST-fusion protein specifically bound to the tethered peptide/protein is determined by ELISA using an anti-GST antibody conjugated to horse radish peroxidase. Compounds which block the interaction between the biotinylated peptide/protein and the GST-fusion protein cause a decrease in the ELISA signal.

In a specific example, an assay was developed to screen for compounds that block the interaction between the Bcl-2 homologs, Bcl-$x_L$ and Bak. A biotinylated Bak GD domain peptide (amino acid residues 71-89; N-biotinylated MGQVGRQLAIIGDDINRRY [SEQ ID NO: 35]) was bound to wells coated with neutravidin. GST-Bcl-$x_L$ was shown to bind specifically to the GD domain peptide and the extent of binding was determined by ELISA. Using this assay, peptides from Bcl-2 family members were identified which block the Bcl-$x_L$/Bak GD domain interaction (FIG. 10). Peptides which encompass the GD domain from Bak, Bax, and Bip1a showed a concentration-dependent inhibition of binding. A mutant Bak peptide with an alanine substitution for leucine at residue 78 and a peptide from the Bcl-2 homolog Bcl-w did not block binding.

3. In Vitro Binding Assay

An in vitro binding assay as described herein can be used to screen for compounds, compositions and agents that disrupt GD domain-mediated interactions.

GST-Bcl-$x_L$, or GST-Bcl-2 is incubated with a labeled GD domain-containing protein in the presence of a test compound. Resulting protein complexes are captured on GSH-agarose beads and the amount of labeled interacting protein is measured. Compounds that block binding will inhibit complex formation.

In a specific example, the inhibition of the interaction of GST-Bcl-$x_L$ and $^{35}$S-methionine-labeled Bak by a 20-amino acid Bak GD domain peptide (amino acid residues 70-89; TMGQVGRQLAIIGDDINRRY; [SEQ ID NO: 36]) is shown in FIG. 11.

4. Cell-based Assay

A method for detection of protein/protein interactions in transfected cells as described herein and shown in FIG. 3B demonstrated that interaction of Bcl-$x_L$, with Bak, Bax, and Bip1a in this assay required the GD domain (FIG. 6). Test compounds, compositions or agents are added to the cell media following transfection, and those which disrupt GD domain-mediated interactions are identified using this assay.

5. Microinjection Assay

As described herein, agents that bind to Bcl-$x_L$, and thereby inhibit its function may comprise "GD domain mimetics." In the present example a method is described for directly screening for such agents. This example demonstrates directly that agents that disrupt GD domain-mediated interactions are capable of modulating apoptosis as described herein.

A cell-based microinjection assay is provided for the identification of agents that antagonize GD domain-mediated interactions and inhibit the cell death suppression activity of Bcl-$x_L$ and/or Bcl-2. One or preferably more than one cells are microinjected with a death suppressor protein, such as Bcl-$x_L$ or Bcl-2, which protects the cells from induction of cell death by an apoptosis-inducing agent, in the presence of a test compound, composition or agent. Compounds that bind to the death suppressor protein and prevent its protective function, resulting in the death of the microinjected cells, can thereby be identified.

In a specific example, microinjection of bacterially-expressed GST-Bcl-$x_L$, but not GST alone, efficiently protected HeLa cells from death induced by Fas ligation (using an anti-FAS antibody) in the presence of cycloheximide (FIG. 12). Co-injection of a 15 amino acid Bak GD domain peptide (Bak-15), which disrupts GD domain-mediated interactions with Bcl-$x_L$ (see FIG. 10), greatly attenuated the protective effect of Bcl-$x_L$ in this assay. A mutant Bak GD domain peptide (Bak-15L78A), in which an alanine was substituted for a leucine at position 78, did not block Bcl-$x_L$-mediated protection from Fas-induced death. The ability of GD domain peptide variants to inhibit the function of Bcl-$x_L$ correlated with their ability to bind to Bcl-$x_L$ (see FIG. 10). Under these conditions, neither peptide had an effect on cell viability in the absence of anti-Fas treatment. Similar results were obtained with MRC5 human diploid fibroblasts where protection from anti-Fas-induced death by microinjected Bcl-$x_L$ was inhibited by co-injection of the wild-type, but not mutant, Bak BH3 peptide.

Microinjection procedure: HeLa cells were plated in complete DMEM in 60 mm dishes at $2.4 \times 10^5$ cells per dish. Mixtures containing peptides and proteins as indicated in 25 mM HEPES buffer, pH 7.2 containing 3.3 mM NaCl and 1 mg/ml FITC-dextran as a marker were filter sterilized and injected into the cytoplasm of cells using an Eppendorf micromanipulator and microinjector with femtotip capillary microtips. Following injection, the cells were returned to the incubator and after 1 hour the number of injected cells was determined by fluorescence microscopy. Cells were then treated with anti-Fas mAb (7C11) and cycloheximide (10 mg/ml) and the recovery of injected cells remaining after 18 hours was determined.

All publications mentioned in this specification are herein incorporated by reference, to the same extent as if each individual publication was specifically and individually indicated to be incorporated by reference.

It will be understood that the invention is capable of further modifications and this application is intended to cover any variations, uses, or adoptions of the invention including such departures from the present disclosure as come within known or customary practice within the art to which the invention pertains, and is intended to be limited only by the appended claims.

What is claimed is:

1. A method of identifying an agent capable of modulating GD domain mediated heterodimerization, comprising carrying out a heterodimerization assay which includes a first polypeptide and a second polypeptide, wherein said first polypeptide consists of SEQ ID NO: 40 and SEQ ID NO: 41, and said second polypeptide is Bcl-$X_L$, and an agent; determining whether said agent inhibits or augments heterodimerization of said first polypeptide to said second polypeptide; wherein if inhibition or augmentation of heterodimerization is determined, it indicates that said agent is capable of modulating GD domain mediated heterodimerization.

2. The method of claim 1, wherein said second polypeptide is labeled.

3. The method of claim 1, wherein said second polypeptide is present in a fusion protein.

4. A method of identifying an agent capable of modulating apoptosis in a cell, comprising assaying an ability of said agent to modulate GD domain mediated heterodimerization between a GD domain of a first polypeptide, wherein said GD domain consists of SEQ ID NO: 40, and a second polypeptide, wherein said second polypeptide is Bcl-$X_L$; wherein the GD domain mediated heterodimerization is defined by an ability of said GD domain to interact with said second polypeptide; and measuring an increase or decrease in the GD domain mediated heterodimerization, thereby identifying said agent capable of modulating apoptosis in a cell.

5. The method of claim 4, wherein the increase in heterodimerization activity represents an increase in apoptosis.

6. The method of claim 4, wherein the decrease in heterodimerization activity represents a decrease in apoptosis.

* * * * *

SEQUENCE LISTING (1) GENERAL INFORMATION:

(iii) NUMBER OF SEQUENCES: 41

-continued

```
(2) INFORMATION FOR SEQ ID NO: 1:

(i) SEQUENCE CHARACTERISTICS:
        (A) LENGTH: 13 amino acid
        (B) TYPE: amino acid
        (D) TOPOLOGY: linear (ii) MOLECULE TYPE: peptide (xi) SEQUENCE DESCRIPTION: SEQ ID NO: 1:

Gly Asp Asp Ile Asn Arg Arg Tyr Asp Ser Glu Phe Gln
                  5                  10

(2) INFORMATION FOR SEQ ID NO: 2:

(i) SEQUENCE CHARACTERISTICS:
        (A) LENGTH: 28 amino acid
        (B) TYPE: amino acid
        (D) TOPOLOGY: linear (ii) MOLECULE TYPE: peptide (xi) SEQUENCE DESCRIPTION: SEQ ID NO: 2:

Pro Ser Ser Thr Met Gly Gln Val Gly Arg Gln Leu Ala Ile Ile Gly
                  5                  10                  15

Asp Asp Ile Asn Arg Arg Tyr Asp Ser Glu Phe Gln
                 20                  25

(2) INFORMATION FOR SEQ ID NO: 3:

(i) SEQUENCE CHARACTERISTICS:
        (A) LENGTH: 31 amino acid
        (B) TYPE: amino acid
        (D) TOPOLOGY: linear (ii) MOLECULE TYPE: peptide (xi) SEQUENCE DESCRIPTION: SEQ ID NO: 3:

Gln Val Gly Arg Gln Leu Ala Ile Ile Gly Asp Asp Ile Asn Arg Arg
                  5                  10                  15

Tyr Asp Ser Glu Phe Gln Thr Met Leu Gln His Leu Gln Pro Thr
                 20                  25                  30

(2) INFORMATION FOR SEQ ID NO: 4:

(i) SEQUENCE CHARACTERISTICS:
        (A) LENGTH: 15 amino acid
        (B) TYPE: amino acid
        (D) TOPOLOGY: linear (ii) MOLECULE TYPE: peptide (xi) SEQUENCE DESCRIPTION: SEQ ID NO: 4:

Leu Ser Glu Cys Leu Lys Arg Ile Gly Asp Glu Leu Asp Ser Asn
                  5                  10                  15

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 5:

Leu Lys Arg Ile Gly Asp Glu Leu Asp
```

(2) INFORMATION FOR SEQ ID NO: 6:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 6:

Gln Asp Ala Ser Thr Lys Lys Leu Ser Glu Cys Leu Lys Arg Ile Gly
              5                  10              15

Asp Glu Leu Asp Ser Asn Met Glu Leu Gln
        20              25

(2) INFORMATION FOR SEQ ID NO: 7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 7:

Leu Ala Leu Arg Leu Ala Cys Ile Gly Asp Glu Met Asp Val Ser
            5                10            15

(2) INFORMATION FOR SEQ ID NO: 8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 8:

Ile Gly Asp Glu Met
            5

(2) INFORMATION FOR SEQ ID NO: 9:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 9:

Cys Met Glu Gly Ser Asp Ala Leu Ala Leu Asp Leu Ala Cys Ile Gly
              5                  10              15

Asp Glu Met Asp Val Ser Leu Arg Ala Pro Arg Leu
        20              25

(2) INFORMATION FOR SEQ ID NO: 10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 10:

```
Val Gly Arg Gln Leu Ala Ile Ile Gly Asp Asp Ile Asn Arg Arg
            5                   10                  15
```

(2) INFORMATION FOR SEQ ID NO: 11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 11:

```
Ala Ala Pro Ala Asp Pro Glu Met Val Thr Leu Pro Leu Val
            5                   10
```

(2) INFORMATION FOR SEQ ID NO: 12:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO: 12:

```
Leu Glu Cys Met Glu Gly Ser Asp Ala Leu Ala Leu Arg Leu Ala Cys
            5                   10                  15
Ile Gly Asp Glu Met Asp Val Ser Leu Arg Ala Pro Arg Leu Ala Gln
                20                  25                  30
Leu Ser Glu Val
        35
```

(2) INFORMATION FOR SEQ ID NO: 13:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO: 13:

```
Val Pro Gln Asp Ala Ser Thr Lys Lys Leu Ser Glu Cys Leu Lys Arg
            5                   10                  15
Ile Gly Asp Glu Leu Asp Ser Asn Met Glu Leu Gln Arg Met Ile Ala
                20                  25                  30
Ala Val
```

(2) INFORMATION FOR SEQ ID NO: 14:

(i) SEQUENCE CHARACTERISTICS:
        (A) LENGTH: 36 base pairs
        (B) TYPE: amino acid
        (D) TOPOLOGY: linear (ii) MOLECULE TYPE: peptide (xi) SEQUENCE DESCRIPTION: SEQ ID NO: 14:

```
Leu Gln Pro Ser Ser Thr Met Gly Gln Val Gly Arg Gln Leu Ala Ile
            5                   10                  15
Ile Gly Asp Asp Ile Asn Arg Arg Tyr Asp Ser Glu Phe Gln Thr Met
                20                  25                  30
Leu Gln His Leu
```

(2) INFORMATION FOR SEQ ID NO: 15:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
CAGGTGGGAC GGCAGCTCGC CATCATCGGG GACGACATCA ACCGACGCTA TGACTCAGAG 60

TTCCAGACCA TGTTGCAGCA CCTGCAGCCC ACG                               93
```

(2) INFORMATION FOR SEQ ID NO: 16:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO: 16:

```
Gln Val Gly Arg Gln Leu Ala Ile Ile Gly Asp Asp Ile Asn Arg Arg
                 5                  10                  15
Tyr Asp Ser Glu Phe Gln Thr Met Leu Gln His Leu Gln Pro Thr
                20                  25                  30
```

(2) INFORMATION FOR SEQ ID NO: 17:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
CCTAGCAGCA CCATGGGGCA GGTGGGACGG CAGCTCGCCA TCATCGGGGA CGACATCAAC 60

CGACGCT ATGACTCAGA GTTCCAG                                        84
```

(2) INFORMATION FOR SEQ ID NO: 18:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 18:

```
Pro Ser Ser Thr Met Gly Gln Val Gly Arg Gln Leu Ala Ile Ile Gly
                 5                  10                  15
Asp Asp Ile Asn Arg Arg Tyr Asp Ser Glu Phe Gln
                20                  25
```

(2) INFORMATION FOR SEQ ID NO: 19:

(i) SEQUENCE CHARACTERISTICS:
        (A) LENGTH: 45 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 19:

GTGGGACGGC AGCTCGCCAT CATCGGGGAC GACATCAACC GACGC               45

(2) INFORMATION FOR SEQ ID NO: 20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 20:

Val Gly Arg Gln Leu Ala Ile Ile Gly Asp Asp Ile Asn Arg Arg
                5                   10                  15

(2) INFORMATION FOR SEQ ID NO: 21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GGGGACGACA TCAACCGACG CTATGACTCA GAGTTCCAG                      39

(2) INFORMATION FOR SEQ ID NO: 22:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 22:

Gly Asp Asp Ile Asn Arg Arg Tyr Asp Ser Glu Phe Gln
                5                   10

(2) INFORMATION FOR SEQ ID NO: 23:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CAGGATGCGT CCACCAAGAA GCTGAGCGAG TGTCTCAAGC GCATCGGGGA CGAACTGGAC 60

AGTAACATGG AGCTGCAG                                             78

(2) INFORMATION FOR SEQ ID NO: 24:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 24:

Gln Asp Ala Ser Thr Lys Lys Leu Ser Glu Cys Leu Lys Arg Ile Gly
                 5                  10                 15

Asp Glu Leu Asp Ser Asn Met Glu Leu Gln
            20                  25

(2) INFORMATION FOR SEQ ID NO: 25:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

CTGAGCGAGT GTCTCAAGCG CATCGGGGAC GAACTGGACA GTAAC                45

(2) INFORMATION FOR SEQ ID NO: 26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 26:

Leu Ser Glu Cys Leu Lys Arg Ile Gly Asp Glu Leu Asp Ser Asn
                 5                  10                 15

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

CTCAAGCGCA TCGGGGACGA ACTGGAC                                    27

(2) INFORMATION FOR SEQ ID NO: 28:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 28:

Leu Lys Arg Ile Gly Asp Glu Leu Asp
                 5

(2) INFORMATION FOR SEQ ID NO: 29:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 29:

TGCATGGAGG GCAGTGACGC ATTGGCCCTG CGGCTGGCCT GCATCGGGGA CGAGATGGAC 60

GTGAGCCTGA GGGCCCCGCG CCTG 84

(2) INFORMATION FOR SEQ ID NO: 30:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 30:

Cys Met Glu Gly Ser Asp Ala Leu Ala Leu Arg Leu Ala Cys Ile Gly
              5                    10                15

Asp Glu Met Asp Val Ser Leu Arg Ala Pro Arg Leu
            20                25

(2) INFORMATION FOR SEQ ID NO: 31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

TTGGCCCTGC GGCTGGCCTG CATCGGGGAC GAGATGGACG TGAGC 45

(2) INFORMATION FOR SEQ ID NO: 32:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 32:

Leu Ala Leu Arg Leu Ala Cys Ile Gly Asp Glu Met Asp Val Ser
              5                    10                15

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

ATCGGGGACG AGATG 15

(2) INFORMATION FOR SEQ ID NO: 34:

(i) SEQUENCE CHARACTERISTICS:
        (A) LENGTH: 5 amino acids
        (B) TYPE: amino acid
        (D) TOPOLOGY: linear (ii) MOLECULE TYPE: peptide

```
    (xi) SEQUENCE DESCRIPTION: SEQ ID NO: 34:

Ile Gly Asp Glu Met
                5

(2) INFORMATION FOR SEQ ID NO: 35:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 35:

Met Gly Gln Val Gly Arg Gln Leu Ala Ile Ile Gly Asp Asp Ile Asn
                5                   10                  15

Arg Arg Tyr (2) INFORMATION FOR SEQ ID NO:36:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 36:

Thr Met Gly Gln Val Gly Arg Gln Leu Ala Ile Ile Gly Asp Asp Ile
                5                   10                  15

Asn Arg Arg Tyr
            20

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 37:

Gln Val Gly Arg Gln Leu Ala Ile Ile Gly Asp Asp Ile Asn Arg
                5                   10                  15

(2) INFORMATION FOR SEQ ID NO:38:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 38:

Gln Val Gly Arg Gln Ala Ala Ile Ile Gly Asp Asp Ile Asn Arg
                5                   10                  15

(2) INFORMATION FOR SEQ ID NO:39:

(i) SEQUENCE CHARACTERISTICS:
        (A) LENGTH: 20 amino acids
        (B) TYPE: amino acid
        (D) TOPOLOGY: linear
```

-continued

```
    (ii) MOLECULE TYPE: peptide (xi) SEQUENCE DESCRIPTION: SEQ ID NO: 39:

Ala Ala Asp Pro Leu His Glu Ala Met Arg Ala Ala Gly Asp Glu Phe
                5                   10                  15

Glu Thr Arg Phe
            20

(2) INFORMATION FOR SEQ ID NO:40:

(i) SEQUENCE CHARACTERISTICS:
          (A) LENGTH: 20 amino acids
          (B) TYPE: amino acid
          (D) TOPOLOGY: linear (ii) MOLECULE TYPE: peptide (xi) SEQUENCE DESCRIPTION: SEQ ID NO: 40:

Ser Thr Lys Lys Leu Ser Glu Cys Leu Lys Arg Ile Gly Asp Glu Leu
                5                   10                  15

Asp Ser Asn His
            20

(2) INFORMATION FOR SEQ ID NO:41:

(i) SEQUENCE CHARACTERISTICS:
          (A) LENGTH: 20 amino acids
          (B) TYPE: amino acid
          (D) TOPOLOGY: linear (ii) MOLECULE TYPE: peptide (xi) SEQUENCE DESCRIPTION: SEQ ID NO: 41:

Gly Ser Asp Ala Leu Ala Leu Arg Leu Ala Cys Ile Gly Asp Glu Met
                5                   10                  15

Asp Val Ser Leu
            20
```